(12) United States Patent
Alcaide et al.

(10) Patent No.: US 11,269,414 B2
(45) Date of Patent: Mar. 8, 2022

(54) BRAIN-COMPUTER INTERFACE WITH HIGH-SPEED EYE TRACKING FEATURES

(71) Applicant: Neurable Inc., Boston, MA (US)

(72) Inventors: Ramses Alcaide, Boston, MA (US); Dereck Padden, Newton, MA (US); Jay Jantz, Burlington, MA (US); James Hamet, Cambridge, MA (US); Jeffrey Morris, Jr., Cambridge, MA (US); Arnaldo Pereira, Somerville, MA (US)

(73) Assignee: Neurable Inc., Boston, MA (US)

( * ) Notice: Subject to any disclaimer, the term of this patent is extended or adjusted under 35 U.S.C. 154(b) by 0 days.

(21) Appl. No.: 16/797,376

(22) Filed: Feb. 21, 2020

(65) Prior Publication Data

US 2020/0192478 A1 Jun. 18, 2020

Related U.S. Application Data

(63) Continuation of application No. PCT/US2018/047598, filed on Aug. 22, 2018.
(Continued)

(51) Int. Cl.
*G06F 3/01* (2006.01)
*A61B 3/113* (2006.01)
(Continued)

(52) U.S. Cl.
CPC .............. *G06F 3/015* (2013.01); *A61B 3/113* (2013.01); *A61B 5/378* (2021.01); *A61B 5/38* (2021.01);
(Continued)

(58) Field of Classification Search
None
See application file for complete search history.

(56) References Cited

U.S. PATENT DOCUMENTS 4,013,068 A 3/1977 Settle et al.
4,158,196 A 6/1979 Crawford, Jr.
(Continued)

FOREIGN PATENT DOCUMENTS

CA 2 765 500 A1 12/2010
CN 1927551 A 3/2007
(Continued)

OTHER PUBLICATIONS

Non-Final Office Action dated Aug. 15, 2019 for U.S. Appl. No. 16/138,791, 12 pages.
(Continued)

*Primary Examiner* — Stephen T. Reed
(74) *Attorney, Agent, or Firm* — Cooley LLP

(57) ABSTRACT

Embodiments described herein relate to systems, devices, and methods for use in the implementation of a brain-computer interface that integrates real-time eye-movement tracking with brain activity tracking to present and update a user interface that is strategically designed for high speed and accuracy of human-machine interaction. Embodiments described herein also relate to the implementation of a hardware agnostic brain-computer interface that uses real-time eye tracking and online analysis of neural signals to mediate user manipulation of machines.

20 Claims, 17 Drawing Sheets

Related U.S. Application Data

(60) Provisional application No. 62/549,253, filed on Aug. 23, 2017.

(51) Int. Cl.

| | | |
|---|---|---|
| *A61B 5/00* | | (2006.01) |
| *G06F 3/0484* | | (2013.01) |
| *A61B 5/38* | | (2021.01) |
| *A61B 5/378* | | (2021.01) |
| *G06F 3/04842* | | (2022.01) |

(52) U.S. Cl.
CPC ............ *A61B 5/6803* (2013.01); *A61B 5/725* (2013.01); *A61B 5/7264* (2013.01); *G06F 3/04842* (2013.01); *G06F 2203/011* (2013.01)

(56) References Cited

U.S. PATENT DOCUMENTS

| | | |
|---|---|---|
| 4,595,990 A | 6/1986 | Garwin et al. |
| 5,137,027 A | 8/1992 | Rosenfeld |
| 5,213,338 A | 5/1993 | Brotz |
| 5,269,325 A | 12/1993 | Robinson et al. |
| 5,325,862 A | 7/1994 | Lewis et al. |
| 5,339,826 A | 8/1994 | Schmidt et al. |
| 5,342,410 A | 8/1994 | Braverman |
| 5,467,777 A | 11/1995 | Farwell |
| 5,638,826 A | 6/1997 | Wolpaw et al. |
| 5,692,517 A | 12/1997 | Junker |
| 5,742,286 A | 4/1998 | Kung et al. |
| 5,899,867 A | 5/1999 | Collura |
| 5,931,908 A | 8/1999 | Gerba et al. |
| 5,967,996 A | 10/1999 | Kadota et al. |
| 5,983,129 A | 11/1999 | Cowan et al. |
| 6,090,051 A | 7/2000 | Marshall |
| 6,323,884 B1 | 11/2001 | Bird et al. |
| 6,380,937 B1 | 4/2002 | Dong et al. |
| 6,712,468 B1 | 3/2004 | Edwards |
| 6,847,844 B2 | 1/2005 | Sun et al. |
| 6,917,370 B2 | 7/2005 | Benton |
| 7,084,884 B1 | 8/2006 | Nelson et al. |
| 7,120,486 B2 | 10/2006 | Leuthardt et al. |
| 7,546,158 B2 | 6/2009 | Allison et al. |
| 7,580,742 B2 | 8/2009 | Tan et al. |
| 7,835,787 B2 | 11/2010 | Sajda et al. |
| 8,155,736 B2 | 4/2012 | Sullivan et al. |
| 8,244,475 B2 | 8/2012 | Aguilar et al. |
| 8,594,814 B2 | 11/2013 | Rovaglio et al. |
| 8,878,785 B1 | 11/2014 | Nordstrom |
| 9,183,560 B2 | 11/2015 | Abelow |
| 9,210,517 B2 | 12/2015 | Pontoppidan et al. |
| 9,389,685 B1 | 7/2016 | Pathirage et al. |
| 9,468,541 B2 | 10/2016 | Contreras-Vidal et al. |
| 9,532,748 B2 | 1/2017 | Denison et al. |
| 9,563,273 B2 | 2/2017 | Mann |
| 9,743,002 B2 | 8/2017 | Wierich |
| 10,664,050 B2 | 5/2020 | Alcaide et al. |
| 2002/0036381 A1 | 3/2002 | Scibetta |
| 2002/0065851 A1 | 5/2002 | Watson et al. |
| 2003/0031457 A1 | 2/2003 | Miomo et al. |
| 2003/0195798 A1 | 10/2003 | Goci |
| 2003/0203342 A1 | 10/2003 | Bowers |
| 2004/0043372 A1 | 3/2004 | Jebb et al. |
| 2004/0092809 A1 | 5/2004 | DeCharms |
| 2004/0169673 A1 | 9/2004 | Crampe et al. |
| 2004/0249302 A1 | 12/2004 | Donoghue et al. |
| 2005/0017870 A1 | 1/2005 | Allison et al. |
| 2005/0046698 A1 | 3/2005 | Knight |
| 2005/0085744 A1 | 4/2005 | Beverina et al. |
| 2005/0131311 A1 | 6/2005 | Leuthardt et al. |
| 2005/0170325 A1 | 8/2005 | Steinberg et al. |
| 2005/0191609 A1 | 9/2005 | Fadel et al. |
| 2005/0222873 A1 | 10/2005 | Nephin et al. |
| 2005/0226505 A1 | 10/2005 | Wilson |
| 2007/0066914 A1 | 3/2007 | Le et al. |
| 2007/0086773 A1 | 4/2007 | Ramsten et al. |
| 2007/0166675 A1 | 7/2007 | Atkins et al. |
| 2007/0166686 A1 | 7/2007 | Foster |
| 2007/0173733 A1 | 7/2007 | Le et al. |
| 2007/0179396 A1 | 8/2007 | Le et al. |
| 2008/0024724 A1 | 1/2008 | Todd |
| 2008/0065468 A1 | 3/2008 | Berg et al. |
| 2008/0218472 A1 | 9/2008 | Breen et al. |
| 2008/0228242 A1 | 9/2008 | Fink et al. |
| 2008/0317206 A1 | 12/2008 | Hiroaki |
| 2009/0099623 A1 | 4/2009 | Bentwich |
| 2009/0125849 A1 | 5/2009 | Bouvin et al. |
| 2009/0175540 A1 | 7/2009 | Dariush et al. |
| 2009/0289895 A1 | 11/2009 | Nakada et al. |
| 2009/0319058 A1 | 12/2009 | Rovaglio et al. |
| 2010/0010391 A1 | 1/2010 | Skelton et al. |
| 2010/0100001 A1* | 4/2010 | Aguilar ................. A61B 5/378 600/544 |
| 2010/0145215 A1 | 6/2010 | Pradeep et al. |
| 2010/0240016 A1 | 9/2010 | Ween et al. |
| 2010/0280403 A1 | 11/2010 | Erdogmus et al. |
| 2010/0317988 A1 | 12/2010 | Yoshihisa et al. |
| 2011/0004089 A1 | 1/2011 | Chou |
| 2011/0148927 A1 | 6/2011 | Tainsh et al. |
| 2011/0152710 A1 | 6/2011 | Kim et al. |
| 2011/0159467 A1 | 6/2011 | Peot et al. |
| 2011/0175932 A1 | 7/2011 | Yu et al. |
| 2011/0301486 A1 | 12/2011 | Van Hek et al. |
| 2012/0019662 A1 | 1/2012 | Maltz et al. |
| 2012/0034583 A1 | 2/2012 | Dujowich et al. |
| 2012/0036097 A1 | 2/2012 | Prokhorov |
| 2012/0044154 A1 | 2/2012 | Black et al. |
| 2012/0150545 A1 | 6/2012 | Simon |
| 2012/0254745 A1 | 10/2012 | SanGiovanni et al. |
| 2012/0287284 A1 | 11/2012 | Jacobsen et al. |
| 2012/0289854 A1 | 11/2012 | Yamada et al. |
| 2012/0296476 A1 | 11/2012 | Cale et al. |
| 2013/0050432 A1 | 2/2013 | Perez et al. |
| 2013/0125027 A1 | 5/2013 | Abovitz |
| 2013/0130799 A1 | 5/2013 | Van Hulle et al. |
| 2013/0169560 A1 | 7/2013 | Cederlund et al. |
| 2013/0335573 A1 | 12/2013 | Forutanpour et al. |
| 2014/0058528 A1 | 2/2014 | Contreras-Vidal et al. |
| 2014/0065594 A1 | 3/2014 | Venable |
| 2014/0223462 A1 | 8/2014 | Aimone et al. |
| 2014/0225918 A1 | 8/2014 | Mittal et al. |
| 2014/0228701 A1 | 8/2014 | Chizeck et al. |
| 2014/0247232 A1 | 9/2014 | George-Svahn et al. |
| 2014/0316230 A1 | 10/2014 | Denison et al. |
| 2014/0320397 A1 | 10/2014 | Hennessey et al. |
| 2014/0320817 A1 | 10/2014 | Kiderman et al. |
| 2014/0347265 A1* | 11/2014 | Aimone ................. G02C 11/10 345/156 |
| 2014/0372957 A1 | 12/2014 | Keane et al. |
| 2015/0042558 A1 | 2/2015 | Massonneau et al. |
| 2015/0199010 A1 | 7/2015 | Coleman et al. |
| 2015/0212576 A1 | 7/2015 | Ambrus et al. |
| 2015/0212695 A1 | 7/2015 | Nordstrom et al. |
| 2015/0338915 A1 | 11/2015 | Publicover et al. |
| 2016/0077547 A1 | 3/2016 | Aimone et al. |
| 2016/0103484 A1 | 4/2016 | Guo et al. |
| 2016/0198091 A1 | 7/2016 | Edwards |
| 2016/0235323 A1 | 8/2016 | Tadi et al. |
| 2016/0253890 A1 | 9/2016 | Rabinowitz et al. |
| 2016/0259519 A1 | 9/2016 | Foss et al. |
| 2017/0078447 A1 | 3/2017 | Hancock et al. |
| 2017/0124928 A1 | 5/2017 | Edwin et al. |
| 2017/0188933 A1 | 7/2017 | Huggins et al. |
| 2017/0290504 A1 | 10/2017 | Khaderi et al. |
| 2017/0316707 A1 | 11/2017 | Lawrenson et al. |
| 2017/0323615 A1 | 11/2017 | Hazra et al. |
| 2018/0039329 A1 | 2/2018 | Tumey |
| 2018/0364810 A1 | 12/2018 | Parshionikar |
| 2019/0286234 A1 | 9/2019 | Condolo |
| 2020/0268296 A1 | 8/2020 | Alcaide et al. |

(56) References Cited

U.S. PATENT DOCUMENTS

| | | | |
|---|---|---|---|
| 2020/0337653 A1 | 10/2020 | Alcaide et al. | |
| 2021/0064128 A1 | 3/2021 | Alcaide et al. | |

FOREIGN PATENT DOCUMENTS

| | | | |
|---|---|---|---|
| CN | 101339455 A | 1/2009 | |
| CN | 101515199 A | 8/2009 | |
| CN | 102098639 A | 6/2011 | |
| CN | 103092340 A | 5/2013 | |
| CN | 103421859 A | 12/2013 | |
| CN | 104837088 A | 8/2015 | |
| JP | H 11-65794 A | 3/1999 | |
| JP | 2002-236957 A | 8/2002 | |
| JP | 2003-058298 A | 2/2003 | |
| JP | 2010-15584 A | 1/2010 | |
| JP | 2012-053656 A | 3/2012 | |
| JP | 2013-004006 A | 1/2013 | |
| KR | 10-1023249 B1 | 3/2011 | |
| KR | 10-1579364 B1 | 12/2015 | |
| RU | 2 627 075 C1 | 8/2017 | |
| WO | WO 02/091119 A2 | 11/2002 | |
| WO | WO 03/037231 A1 | 5/2003 | |
| WO | WO 2004/073485 A2 | 9/2004 | |
| WO | WO 2005/079332 A2 | 9/2005 | |
| WO | WO 2006/051709 A1 | 5/2006 | |
| WO | WO 2009/056650 A1 | 5/2009 | |
| WO | WO 2010/147913 A1 | 12/2010 | |
| WO | WO 2011/105000 A1 | 9/2011 | |
| WO | WO 2011/140303 A1 | 11/2011 | |
| WO | WO 2012/020906 A1 | 2/2012 | |
| WO | WO 2012/071544 A2 | 5/2012 | |
| WO | WO 2013/012739 A1 | 1/2013 | |
| WO | WO 2014/116826 A | 7/2014 | |
| WO | WO 2016/064314 A1 | 4/2016 | |

OTHER PUBLICATIONS

Non-Final Office Action dated Jun. 12, 2019 for U.S. Appl. No. 15/305,030, 10 pages.
Non-Final Office Action dated Jan. 13, 2020 for U.S. Appl. No. 15/305,030, 12 pages.
Partial Supplementary European Search Report dated Jan. 3, 2018 for European Application No. 15799099.5, 13 pages.
Extended European Search Report dated Apr. 19, 2018 for European Application No. 15799099.5, 13 pages.
International Search Report and Written Opinion dated Oct. 22, 2018 for International Application No. PCT/US2018/047598, 17 pages.
International Search Report and Written Opinion dated Jan. 22, 2019 for International Application No. PCT/US2018/060797, 10 pages.
International Search Report and Written Opinion dated Jun. 20, 2019 for International Application No. PCT/US19/14315, 16 pages.
International Search Report and Written Opinion dated Dec. 18, 2019 for International Application No. PCT/US19/51997, 20 pages.
Amyotrophic Lateral Sclerosis (ALS) Fact Sheet, National Institute of Neurological Disorders and Stroke (Jun. 2013), 12 pages.
Aref, A. W., "The P300-Certainty Algorithm: Improving accuracy by withholding erroneous selections," ECNS Conference, Bristol, Tennessee, Sep. 12-16, 2012, p. 79.
Bai, O. et al., "Exploration of computational methods for classification of movement intention during human voluntary movement from single trial EEG," Clin. Neurophysiol., 118:2637-2655 (2007).
Bai, O. et al., "Towards a User-Friendly Brain-Computer Interface: Initial Tests in ALS and PLS Patients," Clin. Neurophysiol., 121:1293-1303 (2010).
Bashashati, A. et al., "A survey of signal processing algorithms in brain-computer interfaces based on electrical brain signals," J. Neural. Eng., 4:R32-R57 (2007).
Cipresso, P. et al., "The combined use of Brain Computer Interface and Eye-Tracking technology for cognitive assessment in Amyo-trophic Lateral Sclerosis," 2011 5th International Conference on Pervasive Computing Technologies for Healthcare and Workshops, Pervasive Health 2011, 5 pages.
Cipresso, P. et al., "The use of P300-based BCIs in amyotrophic lateral sclerosis: from augmentative and alternative communication to cognitive assessment," Brain and Behavior, 2(4):479-498 (2012).
Connolly, J. F. & D'Arcy, R. C., "Innovations in neuropsychological assessment using event-related brain potentials," Int. J. Psychophysiol., 37:31-47 (2000).
Connolly, J. F. et al., "Performance on WISC-III and WAIS-R NI vocabulary subtests assessed with event-related brain potentials: an innovative method of assessment," J. Clin. Exp. Neurophsychol., 21:444-464 (2010).
D'Arcy, R. C. et al., "Electrophysiological assessment of language function following stroke," Clin. Neurophysiol., 114:662-672 (2003).
D'Arcy, R. C. et al., "Evaluation of reading comprehension with neuropsychological and event-related brain potential (ERP) methods," J. Int. Neurophyschol. Soc., 6(5):556-567 (2000).
Hampshire, A. et al., "Assessing residual reasoning ability in overtly non-communicative patients using fMRI," Neuroimage: Clinical, 2:174-183 (2012).
Iverson, I. H. et al., "A brain-computer interface tool to assess cognitive functions in completely paralyzed patients with amyotrophic lateral sclerosis," Clin. Neurophysiol., 119:2214-2223 (2008).
Kübler, A. et al., "Brain-Computer Interfaces and communication in paralysis: extinction of goal directed thinking in completely paralysed patients?" Clin. Neurophysiol., 119:2658-2666 (2008).
Makeig, S. et al., "Evolving Signal Processing for Brain-Computer Interfaces," Proc. of the IEEE, 100:1567-1584 (2012).
Martens, S. M. M. et al., "Overlap and refractory effects in a brain-computer interface speller based on the visual P300 event related potential; Overlap and refractory effects in a BCI speller based on the visual P300 ERP," Journal of Neural Engineering, 6(2):1741-2552 (2009).
Murguialday, R. A. et al., "Brain-Computer Interface for a Prosthetic Hand Using Local Machine Control and Haptic Feedback," 10th International Conference on Rehabilitation Robotics, IEEE, pp. 609-613 (2007).
Naci, L. et al., "Brain-Computer Interfaces for Communication with Nonresponsive Patients," Ann. Neurol, 72:312-323 (2012).
Perego, P. et al., "Cognitive ability assessment by Brain-Computer Interface: Validation of a new assessment method for cognitive abilities," J. Neurosci. Methods, 201:239-250 (2011).
Power, D. et al., "Towards a system-paced near-infrared spectroscopy braincomputer interface: differentiating prefontal activity due to mental arithmetic and mental singing from the no-control state; Towards a system-paced near-infrared spectroscopy brain-computer interface," Journal of Neural Engineering, 8(6):66004 (2011), 14 pages, doi:10.1088/1741-2560/8/6/066004.
Sellers, E. W. & Donchin, E., "A P300-based brain-computer interface: initial tests by ALS patients," Clin. Neurophysiol., 117:528-548 (2006).
Seo, S. et al., "Discrimination of Yes and No Responses by Auditory Stimuli Multiple-choice Questions in Human EEG," International Conference on Convergence Information Technology, IEEE, pp. 1127-1133 (2007).
Thompson, D. E. et al., "Performance assessment in brain-computer interface-based augmentative and alternative communication," BioMedical Engineering Online, 12:43 (2013), 23 pages, doi:10.1186/1475-925X-12-43.
Thompson, D. E. et al., "Classifier-based latency estimation: a novel way to estimate and predict BCI accuracy," J. Neural Eng., 10(1):016006 (2013), 13 pages, doi:10.1088/1741-2560/10/1/016006. Epub Dec. 12, 2012.
Vieru, T., "Brain Computer Interface Can Stimulate the Cortex," Softpedia (Feb. 16, 2010), 4 pages.
Zander, T. O. & Kothe, C., "Towards passive brain-computer interfaces: applying brain-computer interface technology to human-machine systems in general," J. Neural Eng., 8(2):025005 (2011), 5 pages, doi:10.1088/1741-2560/8/2/025005. Epub Mar. 24, 2011.
Non-Final Office Action dated Jul. 28, 2021 for U.S. Appl. No. 16/847,020, 14 pages.

(56) References Cited

OTHER PUBLICATIONS

Non-Final Office Action dated Nov. 19, 2020 for U.S. Appl. No. 15/305,030, 13 pages.
Final Office Action dated Mar. 12, 2021 for U.S. Appl. No. 15/305,030, 13 pages.
Office Action dated Aug. 31, 2021 for U.S. Appl. No. 15/305,030, 17 pages.
International Search Report and Written Opinion dated Aug. 31, 2015 for International Application No. PCT/2015/032192, 9 pages.
Extended European Search Report dated Apr. 19, 2021 for European Application No. 18848298.8, 15 pages.
Extended European Search Report dated Jul. 14, 2021 for European Application No. 18875541.7, 10 pages.
Heun, V. et al., "Smarter Objects: Using AR technology to Program Physical Objects and their Interactions," CH 2013 Extended Abstracts, Apr. 27-May 2, 2013, pp. 961-966 (2013).
Mohsenzadeh, Y. et al., "A State Space Model for Spatial Updating of Remembered Visual Targets during Eye Movements," Frontiers in Systems Nuroscience, vol. 10, May 12, 2016; 10:39, 22 pages; doi:10.3389/fnsys.2016.00039..
Sorger, B. et al., "Another kind of 'BOLD Response': answering multiple-choice questions via online decoded single-trial brain signals," Progress in Brain Research, Chapter 19, vol. 177, pp. 275-292 (2009).

\* cited by examiner

FIG. 5A
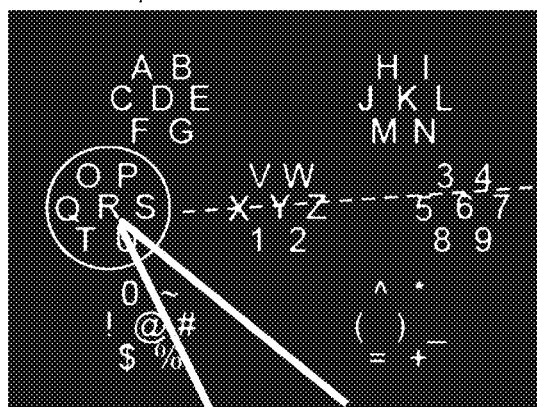
FIG. 5B
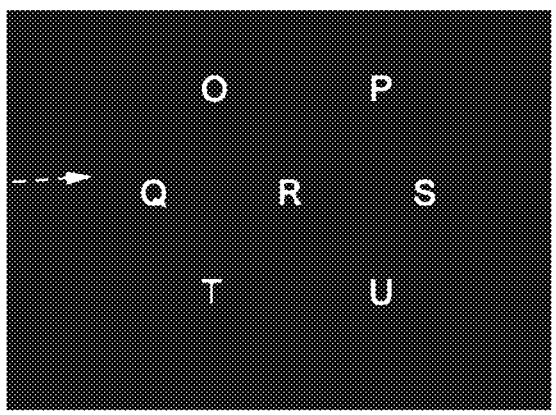
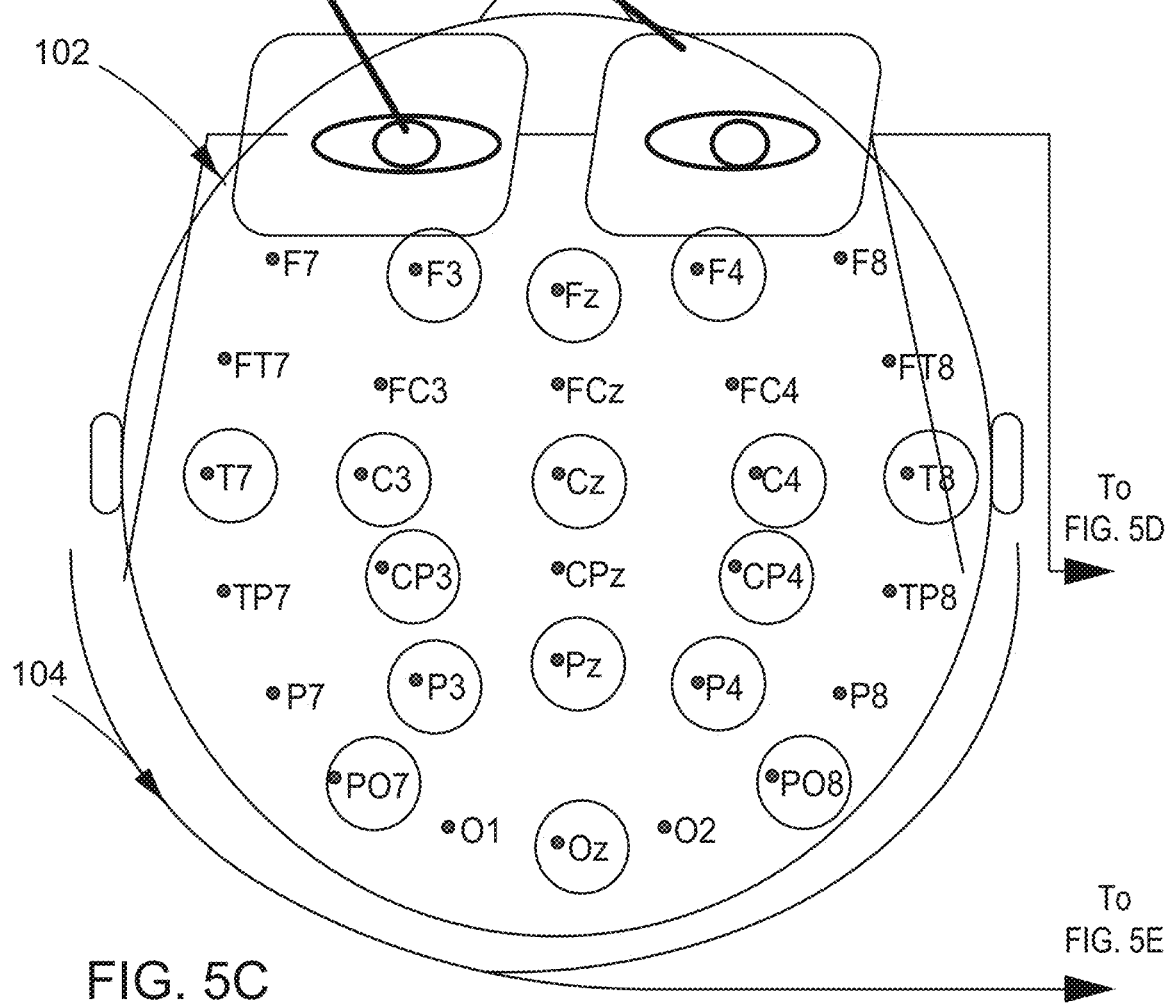
FIG. 5C $T_0$: Object appears. motion noticed
$T_1$: Object Tracking. Dynamic Tag assigned/placed
$T_2$: Tag flash on object
$T_3$: Motion Continues
$T_4$: Tag flash on object
$T_5$: End of object tracking

BRAIN-COMPUTER INTERFACE WITH HIGH-SPEED EYE TRACKING FEATURES

CROSS-REFERENCE TO RELATED APPLICATIONS

This application is a continuation of International Patent Application No. PCT/US2018/047598, filed Aug. 22, 2018 and titled "Brain-Computer Interface with High-Speed Eye Tracking Features," which claims priority to and the benefit of U.S. Provisional Patent Application Ser. No. 62/549,253, entitled "Brain-Computer Interface with High-Speed Eye Tracking Features," filed Aug. 23, 2017, the disclosures of which are hereby incorporated by reference in their entireties.

BACKGROUND

Embodiments described herein relate to systems, devices, and methods for use in the implementation of a brain-computer interface that integrates real-time eye-movement tracking with brain activity tracking to present and update a user interface that is strategically designed for high speed and accuracy of human-machine interaction. Embodiments described herein also relate to the implementation of a hardware agnostic brain-computer interface that uses real-time eye tracking and online analysis of neural activity to mediate user manipulation of machines.

A brain-computer interface (BCI) is a hardware and software communications system that permits brain activity alone to control computers or external devices with direct communication pathways between a wired brain and the external device. BCIs have been mainly designed as an assistive technology to provide access to operating machines and applications directly from interpreting brain signals. One of the main goals of BCI development is to provide communication capabilities to severely disabled people who are totally paralyzed or 'locked in' by neurological neuromuscular disorders, such as amyotrophic lateral sclerosis, brainstem stroke, or spinal cord injury, for whom effective communication with others may be extremely difficult.

Some known implementations of brain computer interfaces include spellers like the one designed by Farwell and Donchin. In this speller, the 26 letters of the alphabet, together with several other symbols and commands, are displayed on-screen in a 6×6 matrix with randomly flashing rows and columns. The user focuses attention on the screen and concentrates successively on the characters to be written, while the neural response of the brain is monitored for signature signals. Once detected the signature signals allow the system to identify the desired symbol. The Farwell-Donchin speller allows healthy people to spell at the rate of about 2 characters per minute.

However, BCIs can be designed to assist even physically able people to operate computers or other data-processing machines and/or software applications without the need for conventional input or output interfaces such as a mouse and a keyboard. BCIs may also provide an interface for more intuitive and natural interaction with a computer than conventional input control. Additionally, BCIs can also be developed to serve many other functions including augmenting, repairing as well as mapping and researching human and animal cognitive and/or sensory motor systems and their functions. Some BCI applications include word processors, adapted web browsers, brain control of a wheelchair or neuroprostheses, and games, among others. However, most applications have solely been designed for training or demonstration purposes.

SUMMARY

Systems, devices and methods are described herein for various embodiments of a hardware-agnostic, integrated oculomotor-neural hybrid brain computer interface (BCI) platform to track eye movements and brain activity to mediate real-time positioning of a user's gaze or attention and selection/activation of desired action. This disclosure presents an integrated hybrid BCI system to address the need for Brain Computer Interfaces that operate with high-speed and accuracy.

BRIEF DESCRIPTION OF THE FIGURES

FIGS. 5A and 5B are illustrations of an example user interface before and after a user selection.

FIG. 5C illustrates a user interacting with the interfaces in FIGS. 5A and 5B through a video based eye-tracker and a neural recording headset.

DETAILED DESCRIPTION

Figure 1:
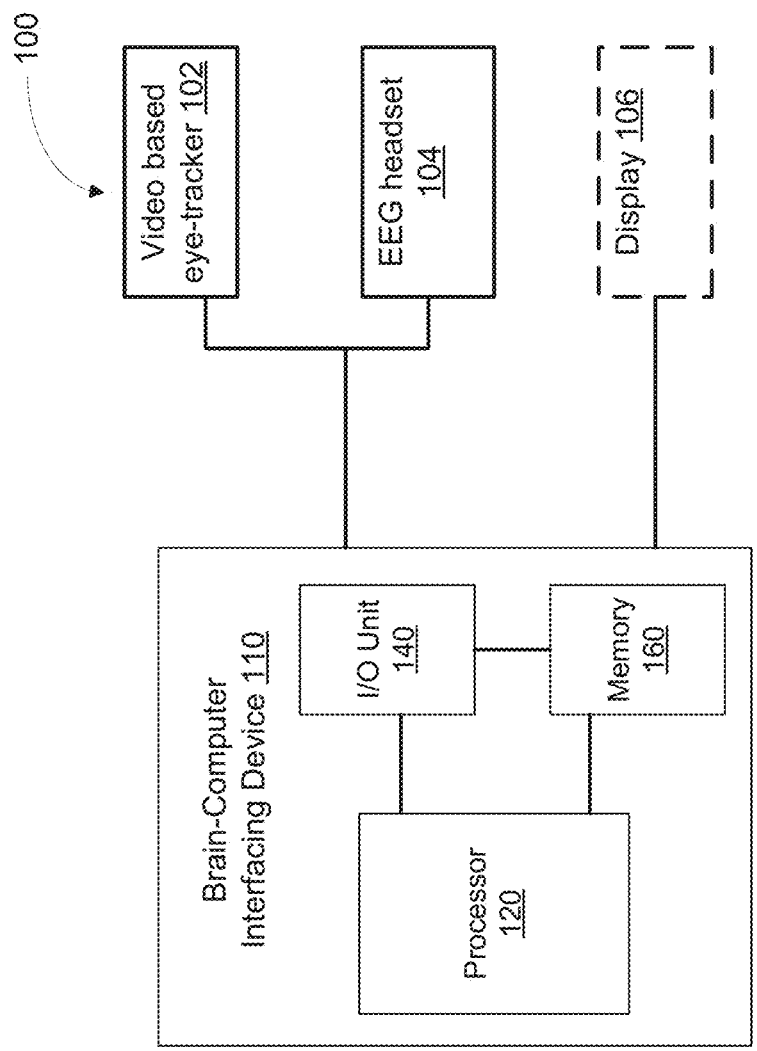
FIG. 1 is a schematic illustration of a hybrid Brain Computer Interfacing system, according to an embodiment.

Embodiments described herein relate to systems, devices, and methods for use in the implementation of a hybrid brain-computer interface (BCI) that integrates real-time eye-movement tracking with brain activity tracking to present and update a user interface that is strategically designed for high speed and accuracy of human-machine interaction. Embodiments described herein also relate to the implementation of a hardware agnostic brain-computer interface that uses real-time eye tracking and online analysis of neural brain signals to mediate user manipulation of machines.

For BCI technology to be better suited for patients, useful to the general public, and employed in the control of real-world tasks, the information transfer rate has to be improved to meet a natural interactive pace, the error rate has to be reduced, and the complexity of the interaction interface has to be minimized, compared to current implementations. Additionally, BCI applications demand a high cognitive load from the users, thus the user interface has to be improved to move away from quiet laboratory environments into the real world. In order to configure BCI devices and applications to be easier and more intuitive, there exists a need for improved devices and techniques in the implementation of brain machine interfaces that operate with high-speed and high accuracy to enable user mediated action selection through a natural intuitive process.

A Hybrid BCI System

As described herein, a BCI is a hardware and software communications system that permits brain activity alone to control computers or external devices. A hybrid BCI system includes a display of stimuli through an interface, a hardware apparatus to locate the point of focus of a user on the interface, a device for recording and processing brain activity, and an apparatus for effecting control of the interface, which may translate into control over the user's environment. These standard features can be characterized as (1) a pointing control feature, (2) an action control feature, and (3) a user interface feature. The pointing control feature can be analogized to a conventional pointing device like a mouse pointer that allows a user to narrow down to a small set of manipulators to control. The action control feature can be analogized to a selection device, for example a mouse click or a keyboard stroke, that allows the user to effect change with an action. The action can be one of many, for example, an activation or a deactivation, a continuous change to the user interface (e.g. scrolling) or an acute change to the user interface with discrete starts and stops (e.g. highlighting, hovering, etc.), pinching, zooming, titling, rotating, swiping, among others. Some other examples of action control via a user interface can include a virtual keyboard control, menu navigation, actions to place and unplace object or items, action to move objects or items, expand and/or shrink objects, movement or navigation of the first person observer or player, changing perspectives of the observer, and actions like grabbing, picking or hovering. Some of these aspects of action control are disclosed below. The user interface feature in a hybrid BCI system can be analogized to an operating system that creates and maintains an environment that implements the pointing and action control features in addition to other features like offering a selection menu, navigation controls, etc.

In some embodiments of a hybrid BCI system described herein, the pointing control feature and methods for identifying a user's point of focus can include an eye-tracking device. In some embodiments, the action control feature and methods for identifying the intent of the user can include any suitable form of monitoring neural signals in the brain. This can include, for example, brain imaging through electrical or optical methods. For example, in some embodiments, the hybrid BCI system can use electrodes recording neural signals of brain activity, channeled through an amplifier and a processor that convert the user's brain signals to BCI commands. In some embodiments, the hybrid BCI systems can implement sophisticated user interfaces that implement brain activity based control of machines. Specific adaptations to one or more of these features can be implemented, as described in detail below, to achieve high speed and accuracy of human interaction with the hybrid BCI system.

FIG. 1 is a schematic illustration of a hybrid Brain Computer Interface system 100, according to an embodiment. The example hybrid Brain Computer Interface system 100 (also referred to herein as "hybrid BCI system" or "BCI system" or "system") is an integrated oculomotor-neural hybrid BCI system that includes a video based eye-tracker 102 and a neural recording headset 104 for recording one or more control signals of the user's brain. The control signals can be any form of neural activity recorded through any suitable approach like electroencephalography (EEG), electrocorticography (ECoG) or magnetoencephalography (MEG), etc. Example forms of neural activity include Event Related Potentials (ERPs), motor imagery, visually evoked Potentials (VEP), brain state dependent signals, etc. The example hybrid BCI system 100 also includes a Brain-Computer Interfacing Device 110, and optionally an audio-visual display 106.

In some embodiments of the hybrid BCI system 100, the user's point of focus can be determined from the video based eye-tracker 102 (i.e., the pointing control feature), and the neural recording headset 104 can be used for collecting neural brain activity data (i.e., the action control feature). The collected neural and eye-tracking data can be communicated to the Brain-Computer Interfacing Device 110 that processes the signals as an ensemble along with data about what stimuli were presented. With the combined information, the Brain-Computer interfacing Device 110 can detect relevant signal features based on statistical models to predict the user's intent. This predicted intent can then be communicated to the user, via the user interface presented through the display 106 for example, and acted upon.

Video Based Eye-Tracking—the Pointing Control Feature

In some embodiments, the video based eye-tracker 102 can be used to determine where a user is looking in their visual field by rapidly following the eye movements of the user in a two or three dimensional space. For example, provided the user has voluntary control of their eye-movements, the video based eye tracer 102 can be used to determine which subspaces in their visual field their eyes are "pointing to." In other words, the video based eye-tracker 102 can use the user's eye-movement trajectories as a pointing control feature, revealing significant information about the subject's intent and behavior. In some embodiments, aspects of where in the visual space their attention focused, what stimulus they are focused upon, or what stimulus they responded to, can be used effectively in the BCI system 100.

Figure 2A:
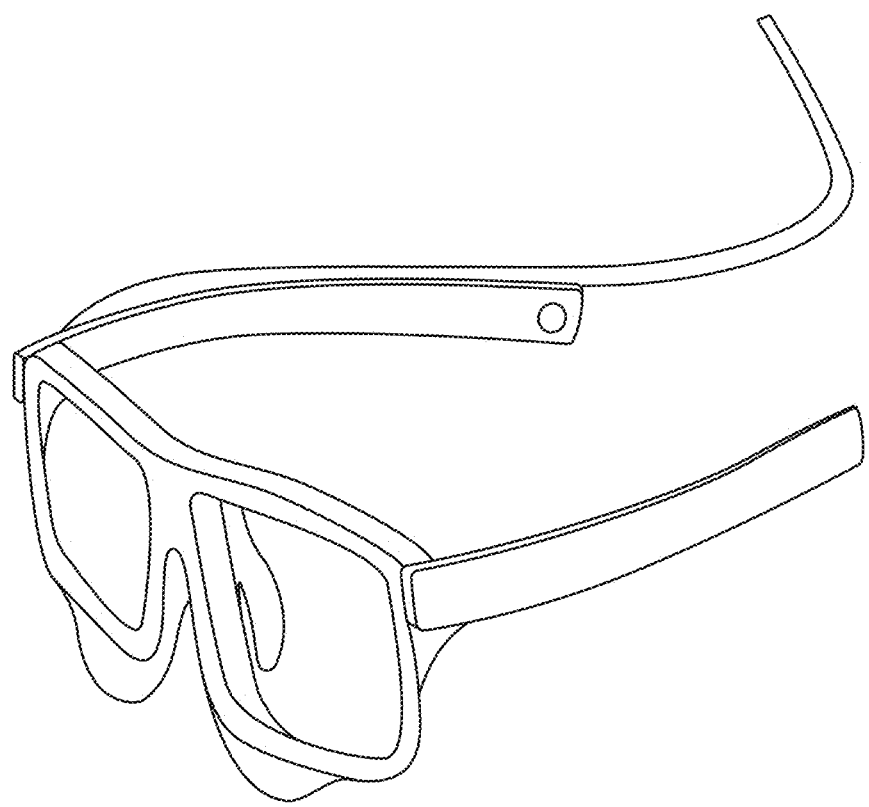
FIG. 2A is an illustration of a video based eye-tracking device.
Figure 2B:
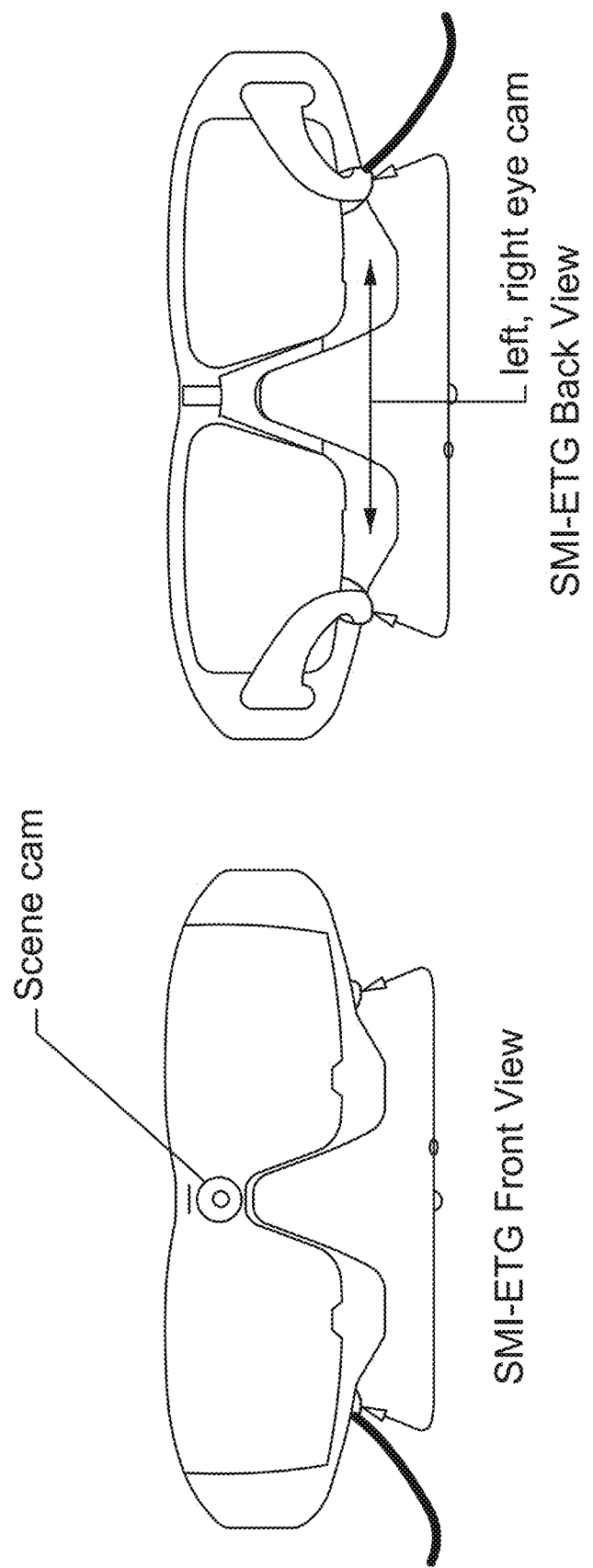
FIG. 2B shows a front and rear view of a video based eye-tracking device.

In some embodiments, the video based eye-tracker 102 relies on tracking the user's pupil and a first-surface corneal reflection (CR) of an illumination source with the use of a head-mounted eye tracking video camera to image the user's eye. The positional difference between these two features can be used to determine the observer's eye-in-head orientation. Some example head mounted eye-tracking devices that can be used as the video based eye-tracker 102, are shown in FIGS. 2A and 2B and are available from SenseMotoric Instruments, Tobii Eye Tracking, and Pupil-labs among other commercial vendors. For example, the illustration in FIG. 2B shows a front and rear view of a video based eye-tracker, with the left and right eye cameras indicated. The cameras can be connected to each other, through a wired or wireless connection. The video based eye-tracker can also include an additional scene camera that captures the uses' field of view.

In some embodiments, the video based eye-tracker 102 simultaneously records an image of the pupil and the corneal reflection of an illumination source. The video based eye-tracker 102 can use a near infrared (IR) illumination source that is optimally reflected by the iris and is invisible to humans so it does not disturb or distract the user. The strong IR reflectance yields high contrast images that are particularly beneficial to pupil detection. In some embodiments, the video based eye-tracker 102 can use a collimated, far range light source whereby parallel rays are emitted from a distant illumination source and collimated by optical components. In some embodiments, the video based eye-tracker 102 can use a non-collimated near-source for illuminating the eye whereby the illumination source is mounted at a finite distance (typically 50 mm or less) from the eye and there is no optical component between the source and the eye to collimate the rays.

As described herein, the video based eye-tracker 102 utilizes the light reflected from the eye, which is sensed by a video camera or some any other suitable optical sensor specially designed for this use. The sensed light is then analyzed to extract eye rotation from changes in reflections. In some embodiments, the video based eye-tracker 102 can use the corneal reflection (i.e., the first Purkinje image) and the center of the pupil as features to track over time. In some embodiments, the video based eye-tracker 102 can use reflections from the front of the cornea (i.e., the first Purkinje image) and the back of the lens (i.e., the fourth Purkinje image) as features to track eye movement in a more sensitive approach. In some embodiments, the video based eye-tracker 102 can use even more sensitive methods of tracking by imaging features inside the eye, such as, for example, the retinal blood vessels, and following the movement of these features as the eye rotates.

In some embodiments, the video based eye-tracker 102 can include an integrated display as described below. The video based eye-tracker 102 integrated with a display 106 can be a system configured to view virtual reality space. In some embodiments, the video based eye-tracker 102 integrated with a display 106 can be configured to view augmented reality space.

Neural Recording of Brain Signals—the Action Control Feature

Central to any BCI system are brain signals that can be used as control signals, making the brain signals an action control feature. Electrophysiological activity, one of the main types of brain activities to be monitored, is generated by electro-chemical transmitters exchanging information between the neurons. The neurons generate ionic currents which flow within and across neuronal assemblies. The large variety of current pathways can be simplified as a dipole conducting current from a source to a sink through the dendritic trunk. These intracellular currents are known as primary currents. Conservation of electric charges dictates that the primary currents are enclosed by extracellular current flows, which are known as secondary currents.

Figure 3A:
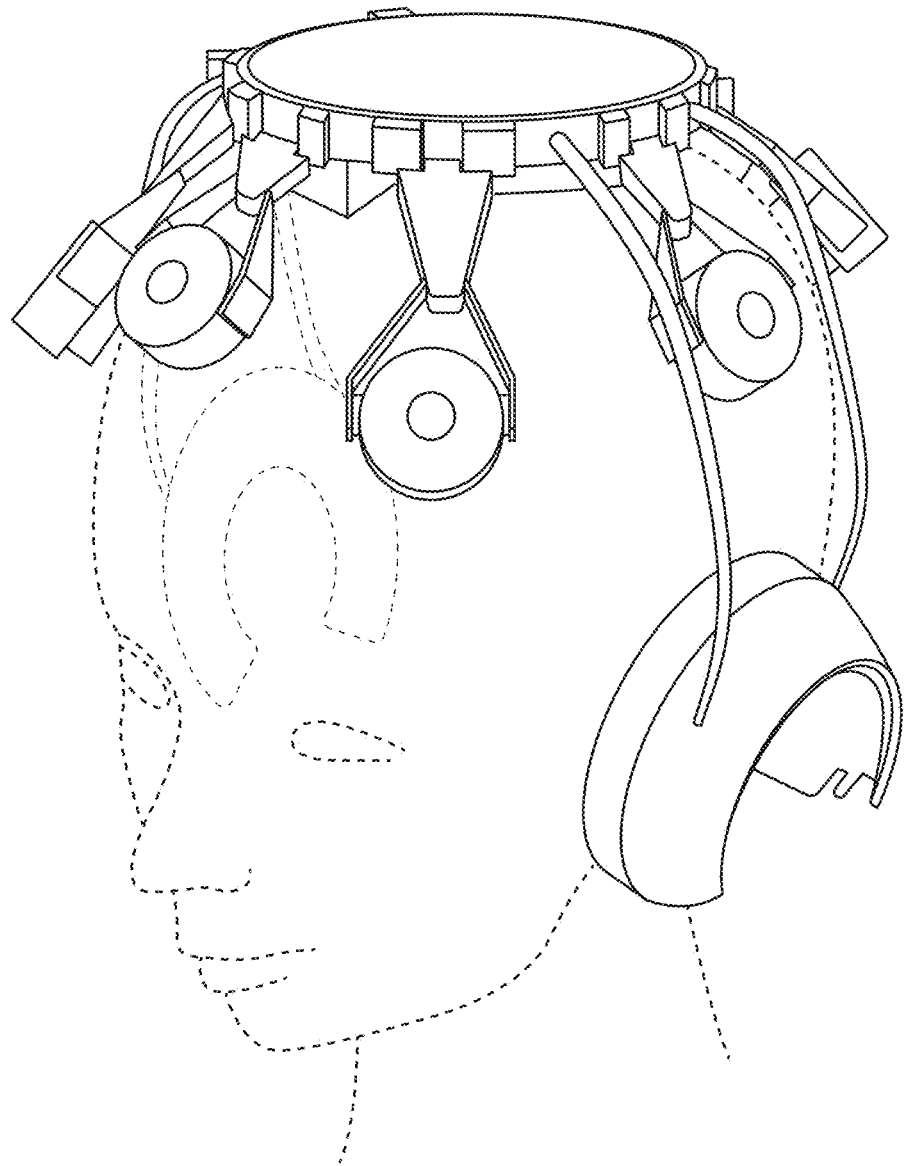
FIG. 3A is an illustration of an exemplary neural recording headset.

As described herein, the neural recording headset 104 uses brain signals to gather information on user intentions through a recording stage that measures brain activity and translates the information into tractable electrical signals that can be converted into commands. In some embodiments, the neural recording headset 104 can be configured to record electrophysiological activity through electroencephalography (EEG) which has a high temporal resolution, low cost of set-up and maintenance, high portability, and is non-invasive to users. The neural recording headset 104 includes a set of electrodes having sensors that acquire electroencephalography signals from different brain areas. These sensors measure electrical neural activity caused by the flow of electric currents during synaptic excitations of the dendrites in the neurons and is extremely sensitive to the effects of secondary currents. The neural signals are recorded through the electrodes appropriately arranged in the neural recording headset 104 and placed on the scalp of a user. An example illustration of an embodiment of the neural recording headset 104 is shown in FIG. 3A, and similar neural recording headsets are available from Biosemi, Wearable Sensing and G.Tec among other commercial vendors.

In some embodiments, the neural recording headset 104 can include electrodes, amplifiers, A/D converter, and a recording device. In some embodiments, the electrodes on the neural recording headset 104 can acquire the signal from the scalp and the amplifiers can magnify the analog signals to enlarge the amplitude of the neural signals. In some embodiments, the one or more electrodes arranged in the neural recording headset 104 can be directly connected to amplifiers, A/D converters, and one or more recording devices to store signals from each electrode. In some embodiments, these components can be housed in the neural recording headset 104. In some embodiments, only the immediate signal amplification can be carried out in the neural recording headset 104 and the other processes like A/D conversion and recording can be carried out after transferring the signal to B-C Integrating Device 110.

Figure 3B:
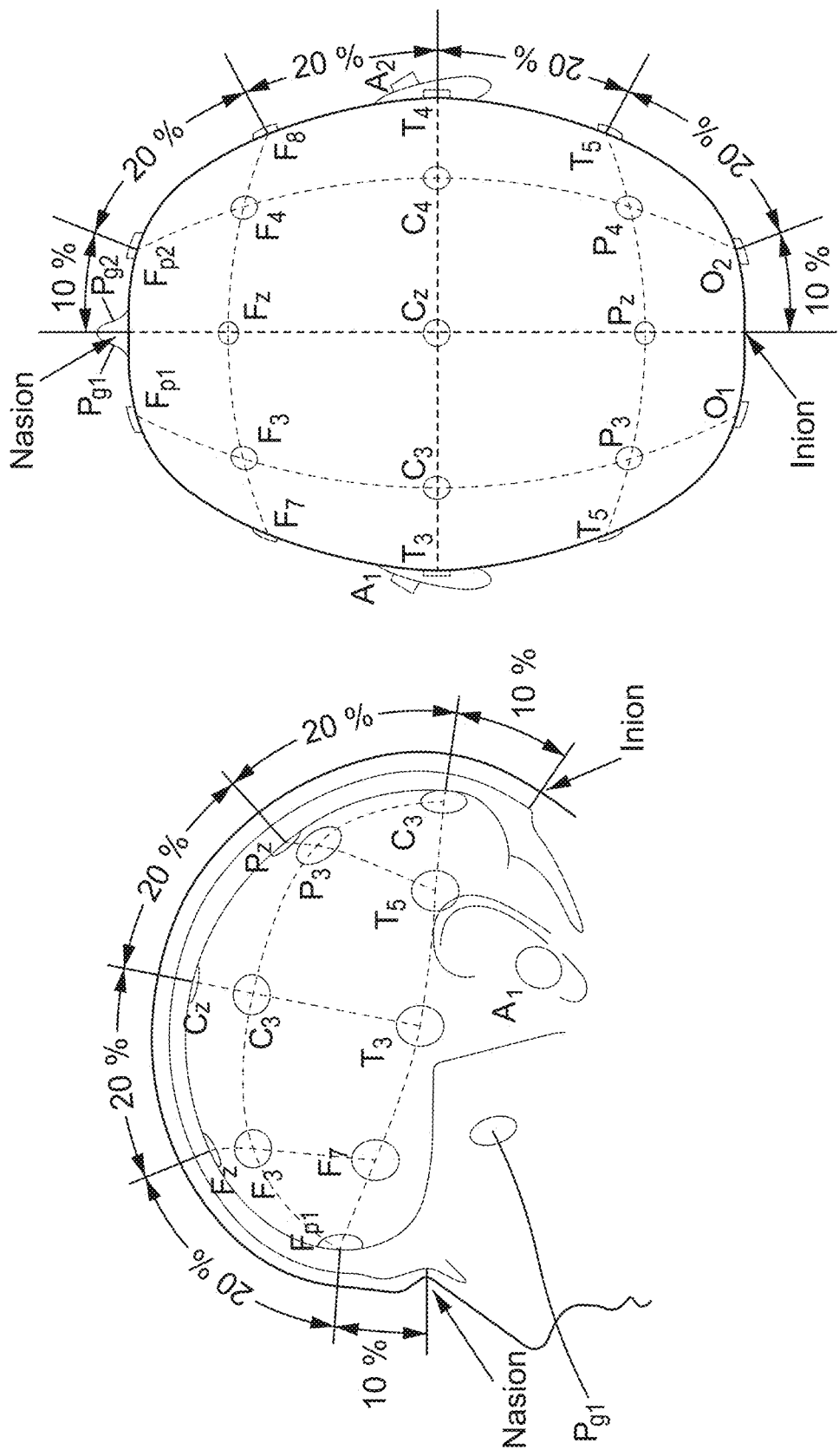
FIG. 3B shows a side view (left) and a top view (right) of example electrode placement locations over the scalp of a user for recording neural brain signals.
Figure 3C:
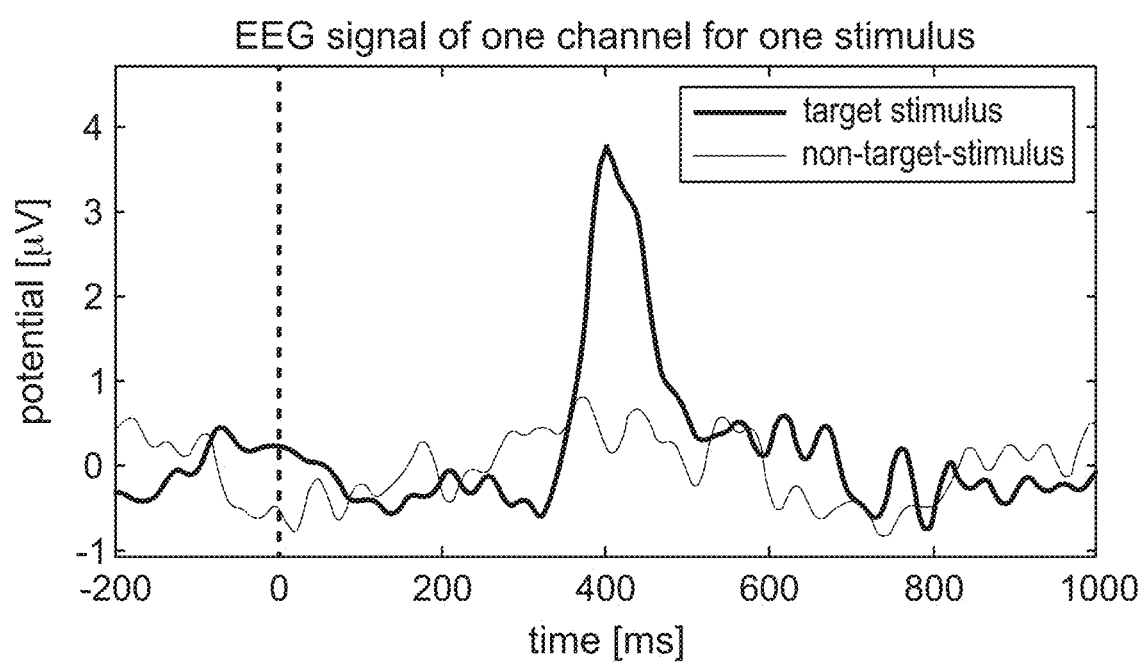
FIG. 3C shows example responses recorded from the brain, indicating the difference between Event Related Potentials (ERPs), a type of neural activity, elicited by a desired target stimulus (black) as opposed to a non-target stimulus (magenta), presented at the time point indicated by the vertical, dashed, line.

In some embodiments, the electrodes on the neural recording headset 104 can be arranged to be placed over the scalp based on the commonly followed International 10-20 system, standardized by the American Electroencephalographic Society. FIG. 3B shows an example illustration of the placement of electrodes according to this system. The 10-20 system uses two reference points on the head to define the electrode location. One of these reference points is the nasion, located at the top of the nose at the same level as the eyes. The other reference point is the inion, which is found in the bony lump at the base of the skull. The transverse and median planes divide the skull from these two points. The electrode locations are determined by marking these planes at intervals of 10% and 20%. The letters in each location correspond to specific brain regions in such a way that A represents the ear lobe, C the central region, Pg the nasopharyngeal, P the parietal, F the frontal, Fp the frontal polar, and O the occipital area. FIG. 3C shows an example set of brain responses following a stimulus, so called stimulus driven "Neural Activity", recorded using the neural recording headset 104. A neural signal is measured as the potential difference over time between an active electrode (also referred to as a signal electrode) and a reference electrode. In some embodiments, a third electrode, known as the ground electrode, can be used to measure the differential voltage between the active and the reference electrodes. In some embodiments, the neural recording headset 104 can include one or more active electrodes, one or more reference electrodes, and one ground electrode. In some embodiments, the neural recording headset 104 can include a few as seven active electrodes. In some embodiments, the neural recording headset can include up to 128 or 256 active electrodes. The electrodes can be made of silver chloride (AgCl) or any other suitable material. The electrodes can be configured so that the electrode-scalp contact impedance can be appropriately adjusted to record an accurate signal. The electrode-tissue interface can be resistive as well as capacitive and it therefore behaves as a low pass filter. The impedance depends on several factors such as the interface layer, electrode surface area, and temperature.

Neural signals recorded non-invasively, across the scalp of a user, have to cross the scalp, skull, and many other layers which can make them weak and hard to acquire. Neural signals can also be affected by background noise generated either within the brain or externally over the scalp, which can impact the ability to extract meaningful information from the recorded signals. Embodiments of the system 100 including the neural recording headset 104 can incorporate several adaptations to improve neural signal acquisition. For example, a gel (i.e., a conductive gel) can be used to create a conductive path between the skin and each electrode to reduce the impedance. In some embodiments, the neural recording headset 104 can include "dry" electrodes that do not need the use of gels, which can be made with other materials such as titanium and stainless-steel. In some embodiments, the neural recording headset 104 can include dry active electrodes with pre-amplification circuits to accommodate the very high electrode/skin interfacial impedances. In some embodiments, the neural recording headset 104 can include dry passive electrodes that do not have any active circuits, but may be linked to a neural recording system configured with ultra-high input impedance.

The amplitude of electrical bio-signals is typically on the order of microvolts. Consequently, the signal is very sensitive to electronic noise. In some embodiments, the BCI system 100 can be designed to reduce the effects of the noise with adaptations such as electromagnetic interference shielding or reduction for common mode signal, amongst others.

Display and Presentation of the User Interface

As described herein, the user interface in the hybrid BCI system 100 functions as a link of communication between the user (e.g., the user's brain, eyes, etc.) and the BC Interfacing Device 110, and enables a user to focus and point at specific stimuli through the pointing control feature and select or deselect specific stimuli using the action control feature. A strategically designed user interface includes a process of presentation of stimuli to a user through any modality, and most commonly though the visual mode. For example, user interfaces can be configured to present a user with visual stimuli, auditory stimuli, haptic stimuli or vestibular stimuli. In some embodiments, a user interface that presents visual stimuli can be rendered on a display like the display 106 shown in FIG. 1.

In some embodiments, the display 106 can be a separate, stand-alone, audio-visual display unit that can be connected and in data communication with the rest of the hybrid BCI system 100. That is, a stand-alone display (e.g., a liquid crystal display) equipped with an audio system (e.g., speakers, or headphones) can be in two-way communication with one or more of the other components of the hybrid BCI system 100, for example, the BC Interfacing Device 110, the video based eye-tracker 102, and the neural recording headset 104. In some embodiments, the display 106 can be integrated into the video based eye-tracker 102 to be part of the eye-glass area. The integrated video based eye-tracker 102 and display 106 can be configured to view virtual reality space in the form of a user interface presented on the display 106. In some embodiments, the integrated video based eye-tracker 102 and display 106 can be configured such that the display 106 is on a semi-transparent eye-glass area, allowing the user to view augmented reality space. That is, the user can view the real-world through the semi-transparent eye-glass area that is also the integrated display 106 presenting the user with a user interface that he/she can interact with.

The Brain-Computer Interfacing Device

In some embodiments, the BC Interfacing Device 110 can be configured to accomplish three main functions. First, the BC Interfacing Device 110 can be configured to generate a strategically designed user interface. For example, the strategically designed user interface can be for a training session or for a testing session. In some embodiments, the user interface can be designed as a virtual reality interface and/or as an augmented reality interface. In some embodiments, the user interface can be tailored for specific needs such as, for example, specific user history, reaction times, user preferences, etc. Second, in addition to designing and generating the user interface, the BC Interfacing Device 110 can be configured to receive the pointing control signal (e.g., from the video based eye-tracker 102) and the action control signal (e.g., from the neural recording headset 104) and processes the signals as an ensemble to determine the user's intent. Finally, the BC Interfacing Device 110 can be configured to implement the pointing control feature and the action control feature by (1) detecting meaningful features from the neural signals, and (2) implementing changes to the stimuli being pointed to per the user's intent. In some embodiments, the BC Interfacing Device 110 can also connected to other peripheral devices that may be a part of the hybrid BCI system 100 such as, for example, peripheral sensors and actuators functioning in modalities other than the visual modality. Such peripheral sensors may include audio microphones, haptic sensors, accelerometers, goniometers etc., and peripheral actuators can include audio speakers, haptic stimulus providers, etc.

In some embodiments, the BC Interfacing Device 110 can include an Input/Output Unit 140 that receives and sends signals from the video based eye-tracker 102, the neural recording headset 104, and the optional audio visual display 106 through one or more data communication ports. The transfer of signals can also be carried out through a wired connection, or wirelessly through any suitable communication channel like Bluetooth, etc. The functions of the Input/Output Unit 140 can include several procedures like signal acquisition, signal preprocessing and/or signal enhancement, etc. The acquired and/or pre-processed signal can be channeled to a processor 120 within the BC Interfacing Device 110. In some embodiments, the processor 120 and its sub-components (not shown) can be configured to handle the incoming data, send and retrieve data to and from a memory 160, and carry out the functions of building and maintaining a user interface which can be rendered on the display 106 or on a display integrated with the video based eye-tracker 102. In some embodiments, the processor 120 and its sub-components can be configured to carry out the functions needed to enable user-specific interpretation of brain signals, and packaging output signals to the Input/Output Unit 140 to be relayed to external devices. Other functions of the processor 120 and its sub-components can include several procedures like feature extraction, classification, and manipulation of the control interface.

Control Signals in the Hybrid BCI System

As described herein, the purpose of the hybrid BCI system 100 is to interpret user intentions by monitoring cerebral activity and locating a control signal that can be used as the action control feature. The formation of user intent can be denoted as a cognitive task. The integrated hybrid BCI system 100 shown in FIG. 1 can use one of several signature brain signals simultaneously evoked by or related to cognitive tasks performed by a user. Some of these brain signals can be decoded in ways that people may learn to modulate them at will. Using these signals, regarded as control signals, can enable the hybrid BCI system 100 to interpret the intentions of the user. Thus, the hybrid BCI system 100 can record and use control signals from the brain and use them as an action control feature controlling the interface between the brain and the computer. Any suitable neural activity can be a control signal used for implementing the action control feature. Some examples of neural activity in time include Event Related Potentials (ERPs), Evoked Potentials (EPs e.g. visually evoked potentials (VEP), auditory evoked potentials, sensory evoked potentials, motor evoked potentials), motor imagery signals, slow cortical potentials, brain state dependent signals and other, as yet undiscovered, signature activity potentials underlying various cognitive or sensorimotor tasks.

As an example form of neural activity, an Event Related Potential or an ERP can be a signature neural activity related to an event or a stimulus presentation correlated in time. ERPs can have distinct shape and features (like the P300 signal known to peak at around 300 ms following the triggering stimulus) that helps with their detection and identification. ERPs can also vary in size and shape across different brain regions and how they map across brain regions can be indicative of specific brain functions and/or user intentions. The neural activity data acquired from the neural recording headset can be analyzed for specific ERP signals and once detected and classified appropriately the BCI Device 110 can implement any particular action associated with the detected ERP on the desired portion of the user interface.

Another example control signals can be the form of Motor Imagery signals which are neural activity signals associated with the user undergoing the mental cognitive process underlying voluntary or involuntary motion. That is, motor imagery signals are brain signals that can be recorded from various brain regions and analyzed by a BCI system 100 while the user imagines the action and/or performs the action. In embodiments where the users are expected to make the bodily movements or gestures, the BCI system can also use information gathered by a set of peripheral sensors coupled to the BCI Device 110, such as goniometers, torsiometers, accelerometers, etc., to help recognize the gesture in high definition during a training session. In some other embodiments, users may not be required to make the physical movements, as it may be sufficient to imagine a set of movements to evoke the motor imagery signals (e.g. after training sessions where a BCI system is allowed to learn associations between a set of movements of a user and a set of motor imagery signals evoked by the movements).

Yet another example of control signals can be in the form of brain state signals or brain state dependent signals. For example, a BCI system can be used to detect patterns or scalp topographies of EEG signals associated with specific attentional states or perceptual states of the brain of a user. Neural activity that can be used by a BCI system can also be the frequency domain. Some examples among others include sensorimotor rhythms, Event Related Spectral Perturbations (ERSPs), specific signal frequency bands like Delta, Theta, Alpha, Beta. Gamma or Mu rhythms etc. One example, the P300 evoked potential, is described below.

P300 Signals

P300 evoked potentials are positive peaks in the neural signal due to infrequent auditory, visual, or somatosensory stimuli. The P300 signal is an "endogenous" brain signal that depends on the processing of the stimulus context and levels of attention and arousal. Without wishing to be bound by any particular theory, the P300 is widely believed to be a neural signature of the mechanisms required to change the mental model of the environment to make an appropriate response. Thus, the P300 signal is an important signature of cognitive processes such as attention and working memory. Advantageously, the use of P300-based BCIs does not require training.

Endogenic P300 responses are elicited about 300 ms (up to 900 ms) after attending to statistically improbable stimuli or what are known as an oddball stimuli among several frequent stimuli. P300 signals can be located over several brain regions and can be indicative of several brain processes. Recordings of brain activity associated with subjects performing controlled tasks with visual targets have shown the occurrence of these consistent, signature signals to be associated with specific stimuli. Target-related responses can occur in the parietal cortex and the cingulate areas of the brain and novelty-related activations can mainly occur in the inferior parietal and prefrontal regions. Stimulus modality-specific contributions come from the inferior temporal and superior parietal cortex for the visual and from the superior temporal cortex for the auditory modality.

This large (>10 μV) positive deflection can occur in participants when they are uncertain about the nature of the upcoming stimulus. The P300 is commonly associated with "oddball" paradigms, in which occasional relevant ("target") stimuli have to be detected in a train of frequent irrelevant "non-target" or "standard" stimuli. The hybrid BCI system 100 can use any neural activity like the P300 signal to determine the relevance of a particular stimulus discriminating it from the others, and to determine the user intent when focusing on that stimulus.

An example P300 signal evoked by a particular target stimulus is shown in FIG. 3C (black trace) compared to the lack of a distinct signal when another non-target stimulus was presented (magenta), recorded using an example neural recording headset 104 of an example system 100. An oddball paradigm presented through an example user interface of the system 100 can reliably yield P300 responses with a parietocentral scalp distribution to target compared to standard stimuli irrespective of stimulus (visual, auditory, somatosensory) or response (button press, counting) modality. P300 responses can also be observed when trains of regular stimuli are interrupted by stimulus omissions, which underlines the endogenous nature of this component.

The amplitude of the P300 can increase with lower probability and higher discriminability of target stimuli. The latency of P300 signals with respect to the onset of the target stimulus can increase when target stimuli are harder to discriminate from standard stimuli but not when response times increase for other reasons. P300 latency is thus an attractive tool to separate the mental chronometry of stimulus evaluation from response selection and execution. The occurrence of P300 signals and their association with specific stimuli can be utilized by the system 100 as an action control feature to select the P300 eliciting stimulus over the non-eliciting one.

Figure 4:
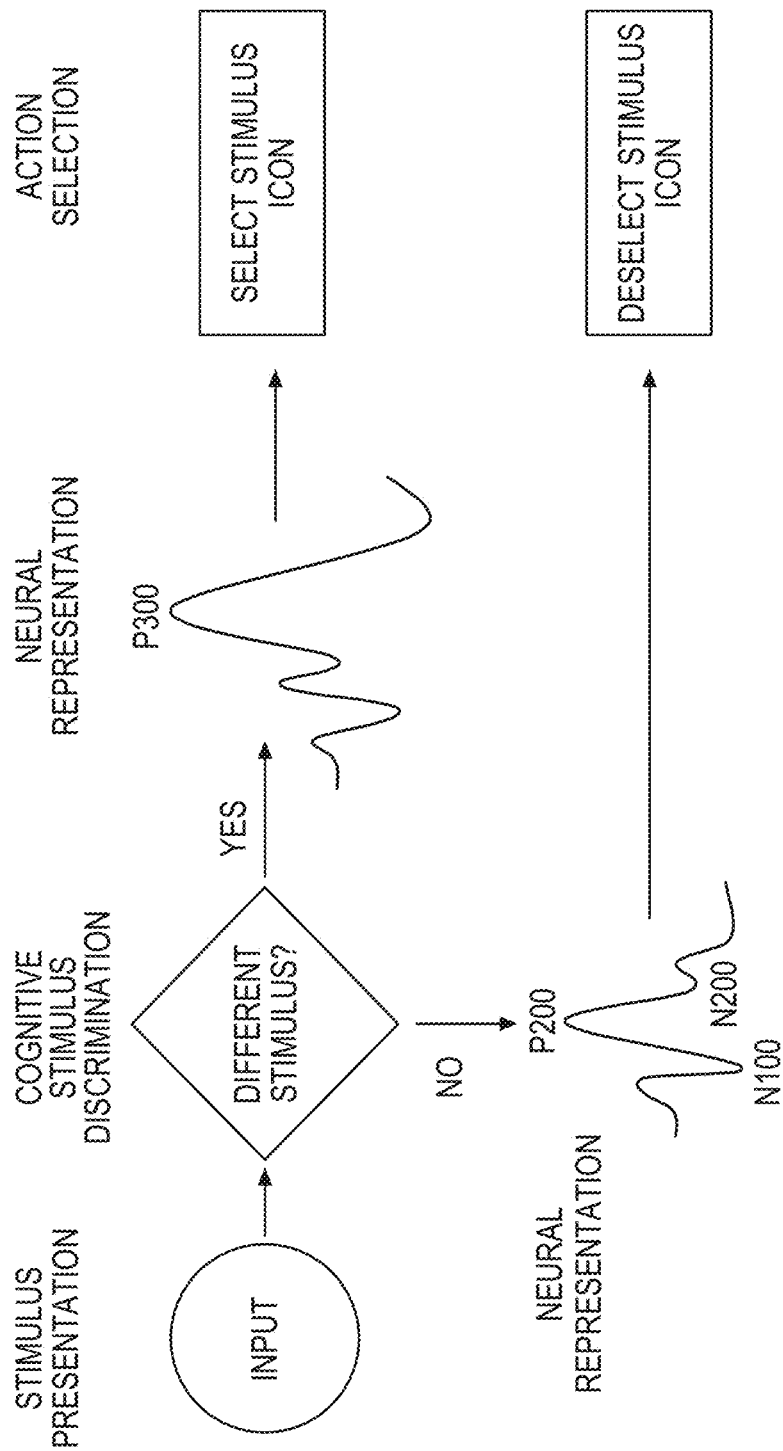
FIG. 4 is a schematic illustration of an example hybrid BCI system using an example stimulus driver neural activity (a P300 signal), to discriminate stimuli and select or deselect a stimulus based on user intent.

FIG. 4A shows a flowchart illustration of an example instance of how a neural activity can be used as a action control feature during the operation of the hybrid BCI system 100, according to an embodiment. In some embodiments, the P300 signal can the neural activity used to determine and act upon a user's intent to select one stimulus over another by distinguishing the first from the second stimulus (as a change or difference). The presence and absence of a P300 signal in the recorded responses can be used to make the selection.

In some embodiments, the hybrid BCI system 100 can be used to manipulate the presentation of various stimuli on the display 106 through the user interface and determine the users intent based on the recorded brain signals over several brain regions following stimulus presentation. Neural activity can vary in shape and size over various brain regions. For example, the parietocentral P300 or P3b is elicited by task-relevant deviant stimuli that are attended to, deviant stimuli that are irrelevant for the task but more salient than the targets elicit a slightly earlier positive deflection that has a frontocentral scalp topography. This novelty P300 or P3a component can be elicited by inserting unique and highly salient ("novel") stimuli in the trains of repeated standard and target events (e.g., visual fractals in trains of simple geometrical figures). However, a similar P3a component can also be elicited by highly discrepant repeated distractors in paradigms that use a difficult target/standard discrimination.

VEP Signals

Visually evoked potential (VEP) signals are brain activity modulations that occur in the visual cortex after receiving a visual stimulus. These modulations are relatively easy to detect due to the large amplitude of VEPs as the stimulus is moved closer to the central visual field. In the hybrid BCI system 100 disclosed herein, VEPs can be used in conjunction with the eye-tracking input, to adopt an integrated approach to enabling the pointing control feature.

VEPs can be classified as transient VEPs (TVEPs) and as steady-state VEPs (SSVEPs). TVEPs occur when the frequency of visual stimulation is below 6 Hz, while SSVEPs occur in reaction to stimuli of a higher frequency. TVEPs can be elicited by any change in the visual field, for example flashing lights, patterns turned on or off, or abruptly reversed in their contrast. TVEPs vary with the stimulus presented and are rarely used in BCI systems.

SSVEPs, more commonly in use with BCI systems, are elicited by visual stimuli changing at a frequency higher than 6 Hz. If the stimulus is a flash, SSVEP shows a sinusoidal-like waveform, the fundamental frequency of which is the same as the blinking frequency of the stimulus. If the stimulus is a pattern, the SSVEP occurs at the reversal rate and at their harmonics. In contrast to TVEP, constituent discrete frequency components of SSVEPs remain closely constant in amplitude and phase over long periods of time. SSVEPs are less susceptible than TVEPs to artifacts produced by blinks and eye movements and to electromyographic noise contamination.

Hybrid BCI System: The Integrated Approach

As described herein, video based eye-tracking can be used in conjunction with neural activity in the form of VEPs or ERPs or other forms of neural activity to enable the pointing control feature and using neural activity as control signals (for example ERPs, or sensorimotor signals, motor imagery signals, brain state signals, etc.) to enable the action control feature. The BC Interfacing Device 110 can be configured to process the integrated signals as an ensemble. In some embodiments, the hybrid BCI system 100 can use SSVEP signals from the neural recording headset 104 in addition to the eye-tracking signal from the video based eye-tracker 102 to have an integrated, hybrid approach to locating the point of gaze of a user. That is, in some embodiments, the video based eye-tracker 102 can be used to detect any suitable form of eye movement information, for example, saccadic, foveation and/or pupil dilation information, as well as foveation information, through oculomotor data conveying movement of the eye muscles. Information about saccadic eye position can also be indirectly obtained from neural activity, for example, ERPs that are evoked by visual responses, acquired from the neural recording headset 104. For example, the hybrid BCI system 100 can be configured to correlate the occurrence of ERPs with the presentation of a particular stimulus in time and space to form a causal relationship. Thus, oculomotor data from the video based eye-tracker 102 can be combined with data from visually evoked neural activity and the strategic presentation of stimuli in the user interface delivered through the display.

An integrated hybrid approach to tracking eye movements allows a user to rapidly select a target by voluntary movement of their eye-gaze, with signals from the video based eye-tracker 102 and the visually evoked neural activity complementing each other in the information provided to locate gaze, as the pointing control feature. The user visually fixes attention on a target and the BC Interfacing Device 110 can identify the target through features analysis of the neural activity, and feature analysis of the video based eye-tracker signal. Notably, in the hybrid BCI system 100, the signals from the video based eye-tracker 102 and the neural recording headset 104 are analyzed as an ensemble, with appropriate weighting for each signal source, by the BC Interfacing Device 110.

For example, the hybrid BCI system 100 can utilize visually evoked neural activity elicited by particular stimuli that may be desired by the user, recorded by the neural recording headset 104. The user interface presented on a visual display (e.g., the display 106) can include a matrix of symbols or commands in specific arrangements. For example, the symbols can be arranged in rows and columns and the rows or columns of this matrix can be flashed at random while the neural signals are monitored. As the user gazes at the desired symbol, the neural activity can be elicited only when the row or column containing the desired symbol flashes. The hybrid BCI system 100 can use data from the video based eye-tracker 102 (i.e., the eye-movement data) and data from the neural recording headset 104 (i.e., the stimulus presentation data) to implement a pointing control feature in order to triangulate and rapidly locate and determine the target symbol desirable to the user.

The hybrid BCI system 100 can use an ensemble processing technique to determine the desired target stimulus. The ensemble processing technique can simultaneously process signals from one or more sources of information available, including eye position, stimulus presentation, neural activity and brain signals associated with visual responses by weighting them appropriately. Upon locating and determining the desired target symbol, the hybrid BCI system 100 can use the recorded neural activity (e.g., a P300 signal) to implement the action control feature.

For example, in some other embodiments of the hybrid BCI system 100, operating under one or more modes, the action control feature can be implemented to select stimuli based only on the stimulus presentation at the time that a neural activity is elicited, regardless of the position of the eye position at the time. In this mode, the weighting of signals may be skewed in favor of the stimulus presentation information during ensemble processing.

Alternatively, in some embodiments, the action control feature can be implemented in one or more modes wherein the hybrid BCI system selects any feature that the users gaze may be upon, at the time-point when a neural activity is detected (accounting for suitable user response times and reaction delays). Thus, any symbol or stimulus that the user's gaze passes over when the neural activity is detected will be selected regardless of which stimulus may have caused the neural activity to be elicited. This feature can be implemented by altering the weights in favor of the eye-position signal to determine which stimulus to select during ensemble processing. Embodiments of the hybrid BCI system 100 can include operational modes capable of both scenarios presented above and other intermediate modes that can also operate in between these example modes by suitably altering the weighting given to the various signals used, for example, the eye-position signals, the stimulus presentation information (including properties of the stimulus, spatiotemporal aspects of presentation, sequence of presentation, etc.) and the neural activity recorded. The hybrid BCI system 100 can also use other sources of information including biological models of the eye of the user, likelihood estimates of a particular neural activity being generated by a particular stimulus based on prior information or cumulative information gathered in real-time).

In some embodiments, the arranged symbols can be flashed several times in different combinations to sample the user's choice multiple times. The signals from each combination can then be averaged to improve the accuracy of detecting the correct symbol. Visual symbols can be accompanied by stimuli of other modalities like auditory or haptic stimuli.

In BCI systems generally, repetition of trials can be cumbersome and slow down the process of selection using neural activity signals like the P300. However, reducing repetitions may risk lowering the accuracy of the selection. In the hybrid BCI system 100 described herein, the accuracy of neural activity-based selection can be improved while maintaining few repeated trials by using sophisticated classifiers as described below. The detection accuracy of visually evoked neural activity and the user experience in general can also be improved by optimizing the properties of stimulus presentation (e.g. display of visual symbols) and by choosing and varying appropriate properties of stimuli (e.g. dimensions or colors of the symbols, their arrangement etc.). Experience can also be improved by configuring the user interface to use specific feedback from the user to predict behavior.

One of the advantages of using the video based eye-tracker 102 in addition to neural activity from the neural recording headset 104 is that the eye movement can be analyzed very rapidly while maintaining robust signal acquisition. By implementing sophisticated analytical routines the position of a user's gaze and focus can be processed in real-time. Further, the video based eye-tracker 102 may not be susceptible to the same noise sources as neural activity recorded through the neural recording headset 104. Processing eye movements using both neural activity as well as video based eye-tracker signals in an integrated approach as described herein can provide a more robust signal amenable to the high-speed and high-accuracy interface that is desirable. In this configuration, one channel can compensate for the weaknesses of the other. Furthermore, the approach of processing both data sets as an ensemble allows the appropriate weighting of the individual signals according to other parameters like user history and specific details of the interface navigated, etc.

In some embodiments, the oculomotor response can be used to change stimulus presentation sequences. Visually evoked neural activity while having a high accuracy of eye movement detection require repeated flashing of stimulus. This may have unpleasant effects on the user experience. To avoid this the hybrid BCI system 100 can, for example, estimate the quadrant of focus of the user from the oculomotor information and reduce or restrict the number of visual stimuli that have to be flashed to that quadrant of the display. Thus flashing of subsections of the display can be linked to a saccade and flashing can be triggered only after a saccade to that location.

User Interaction with the Hybrid BCI System

FIGS. 5A-5E illustrates a user's interaction with the hybrid BCI system 100, according to an embodiment. In this example, the hybrid BCI system 100 is being used to spell words in a two-step process, and the display 106 presents several sub-groupings of characters (e.g., letters, numbers and symbols commonly found on a keyboard) in FIG. 5A. The user wears a video based eye tracker 102 and a neural recording headset 104, shown in FIG. 5C. When the user focuses their gaze on a sub-group containing the desired letter (e.g., the sub-group indicated by the highlighted circle in FIG. 5A), the user interface presented in the display 106 changes to that shown in FIG. 5B where focused sub-group is magnified. The user can then perform the action of selecting a letter by focusing their gaze on the specific desired letter in that sub-group. The action control feature is then implemented by using the neural activity recorded to perform the selection of a letter to be used in forming a word or a sentence.

Figure 5D:
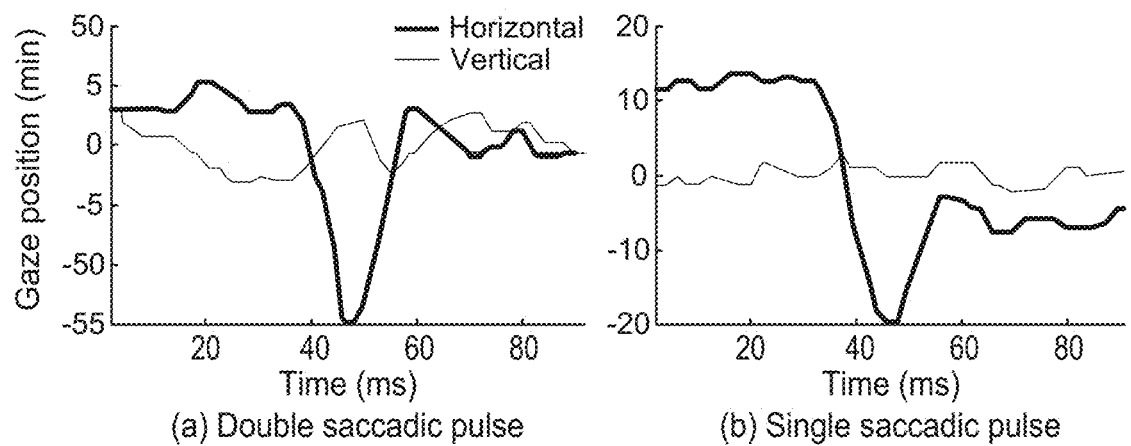
FIGS. 5D and 5E show example signals generated and recorded by the video based eye-tracker and the neural recording headset monitoring brain activity shown in FIG. 5C.
Figure 5E:
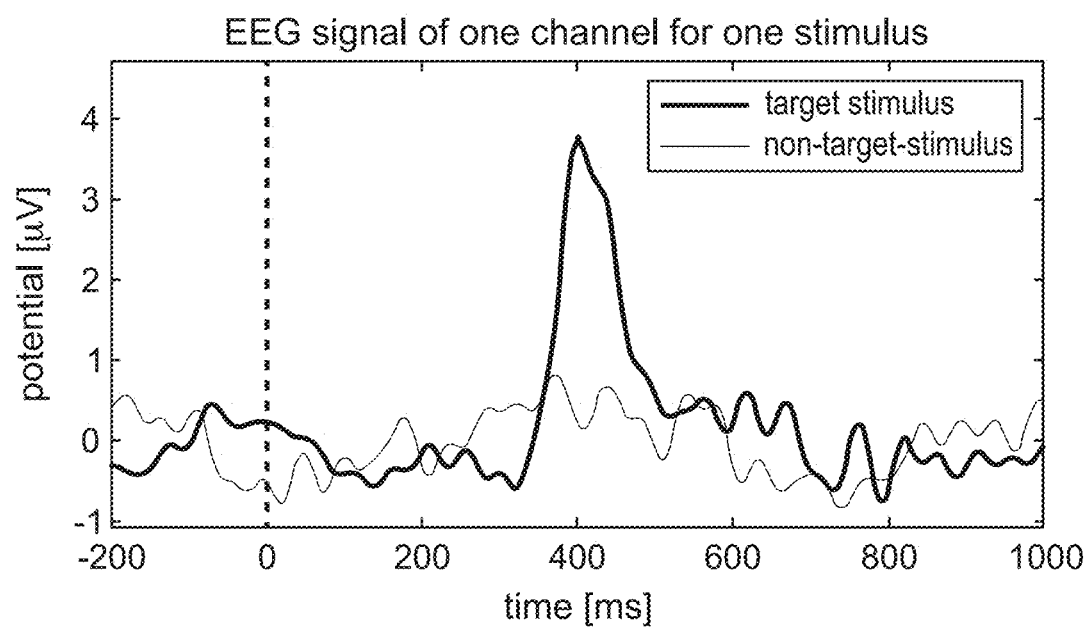

The pointing control feature described above with reference to FIGS. 5A and 5B, is implemented with the video based eye-tracker 102 shown in FIG. 5C. The video based eye-tracker 102 is configured to detect where the user is focusing their gaze, and then output a signal as shown, for example, in FIG. 5D. The action control feature (i.e., activation) is implemented with the neural recording headset 104 shown in FIG. 5C. The neural recording headset 104 is configured to record neural signals from the user's brain, and then output a signal as shown, for example, in FIG. 5E. A processor (not shown) can then extract meaningful features from the eye-tracking signal (FIG. 5D) and the neural signal (FIG. 5E) as an ensemble, and analyze them either in an unsupervised and/or semisupervised manner or by classifying the signals based on prior models built through rigorous training with each specific user. The analyzed data can then be used to make predictions of user behavior such as the point of focus of the user and/or the selection or activation of a symbol upon which focus is predicted.

Figure 5F:
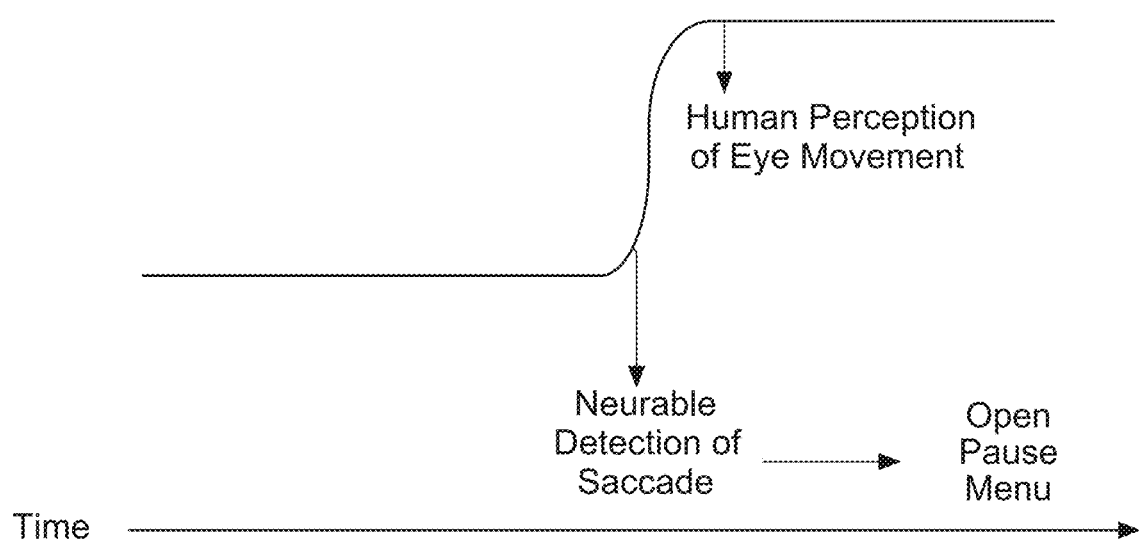
FIG. 5F illustrates the operation of a high-speed eye-movement tracking system that can be implemented to initiate and implement a desired action even before the subject consciously perceived their decision.

FIG. 5F shows an example flow of events in time following video-based eye tracking. In some embodiments, as shown in the example in FIG. 5F, the saccadic eye movement can be detected by the hybrid BCI system even before the conscious perception of self-movement by the user. That is, eye movements can be detected online as they occur immediately after or even before the user's conscious decision. For example, the user may be focused on one grouping of letters as shown in FIG. 5A and may begin to make an eye movement towards another grouping. Even before they consciously realize their own movement a hybrid BCI system disclosed here can detect and use the eye movement to adapt the user interface as is appropriate, which in this case is magnifying the next grouping of letters.

An Example Hybrid BCI System

Figure 6:
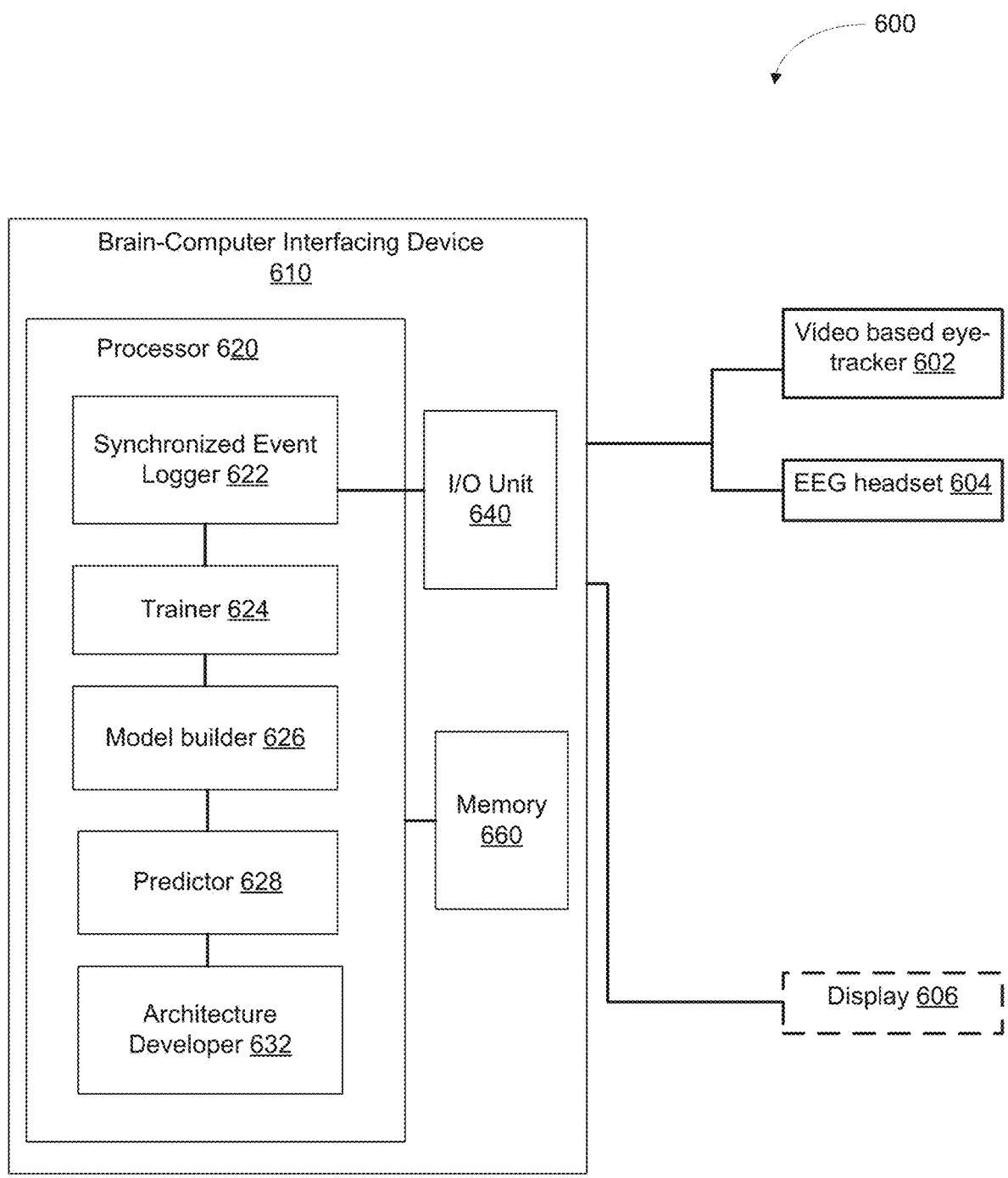
FIG. 6 is a schematic illustration of a hybrid Brain Computer Interfacing Device, according to an embodiment.

FIG. 6 shows a hybrid BCI system 600 according to an embodiment. In some embodiments, the BCI system 600 can be similar in structure and/or function to the corresponding portions of the hybrid BCI system 100 described above with reference to FIG. 1. For example, the BCI system 600 includes a video based eye-tracker 606, an neural recording headset 604, an optional display 606, and a Brain-Computer Interfacing Device 610 that can be the same or similar to the video based eye-tracker 106, the neural recording headset 104, the optional display 106, and the Brain-Computer Interfacing Device 110 of the hybrid BCI system 100. Accordingly, such similar portions and/or aspects are not described in further detail herein.

In some embodiments, a processor 620 of the Brain-Computer Interfacing Device 610 can include a Synchronized Event Logger 622 that receives the eye-tracking and neural signal data via an L/O unit 640, and timestamps the signal data to be synchronous with each other. In some embodiments, the Synchronized Event Logger 622 can be configured to perform high speed eye movement classification.

Gaze signals can be decomposed into saccadic (short duration) and foveation (longer duration) periods. These different components of gaze can be better utilized if the temporal lag inherent in the currently standard threshold-based saccade detection algorithms can be overcome. In addition, video based eye-trackers can be associated with non-physiological artifact, in particular related to blinks, and camera movement with respect to the eye. To overcome these limitations among others, in some embodiments the Synchronized Event Logger 622 can incorporate a probabilistic filtration system with custom machine learning algorithms to allow high speed eye movement detection while minimizing eye-tracker camera sampling rate requirements. Specifically, the Synchronized Event Logger 622 can implement a lag-less filter combined with a machine learning classifier that requires no explicit training and can detect saccades in real-time within 2 microseconds of movement initiation.

Typically, any smoothing function over a times series (e.g., Butterworth filter, moving average, filters) as implemented by currently available BCIs introduce a lag in the smoothed values compared to the actual measured values, preventing a high speed real-time gaze classification system. In some embodiments, the Brain-Computer Interfacing Device 610 as described herein can use a non-linear generative model that estimates gaze as a dynamical system, with state and measurement models based on gaze kinematics and technical parameters of video based eye-trackers. In some embodiments, dual estimation, based on the dual Kalman filter, can be used in order to estimate hidden states of noisy gaze data and approximate the underlying system model. Such an implementation can allow a filtration of gaze data without introducing temporal lag. Additionally, a theoretical gaze kinematics model can be used to estimate missing gaze data when camera sampling rate is lowered, or when transient artifacts occur. Simultaneously, this results in a machine leaning classification system that is automatically trained without the users' explicit knowledge, detecting eye movements in real-time during the movement but not after.

In some embodiments, the Synchronized Event Logger 622 can be configured to implement ensemble estimation of attention using disparate physiological signals as described in examples of the integrated approach. In some embodiments, the Synchronized Event Logger 622 can be configured to implement an analytical pipeline that uses: (1) a Bayesian linear discriminant system, (2) state-of-the-art preprocessing, (3) spatial filtering, (4) a bagging ensemble classifier algorithm, and (5) a higher-order oracle algorithm that incorporates information from the classification algorithm with program routines during the experimental task, to improve selection accuracy. The Brain-Computer Interfacing Device 610 can also be configured to use parallelization and asynchronous processing of separable components in the pipeline to ensure performance on consumer-level personal computers.

In some embodiments, the Synchronized Event Logger 622 can be configured for real-time processing of the oculomotor-neural data in the collected ensemble to detect user intent as described herein. For example, each visual stimulus presented can evoke a signature neural activity (e.g., a P300 signal) captured by the neural recording headset 604. As described herein, the neural activity can act as a control signal indicating a user's attention to a stimulus and intent to act, and the probability of overt attention at a particular visual stimulus or tag can be estimated according a neural activity classification score for each visual stimulus or tag. There can be a decay in the signal associated with a stimulus that reflects spatial uncertainty as well as overt attention based on the degrees in visual space centered on gaze fixation, according to the receptive field of the high fidelity foveal region in the retina. Quantification of the neural activity score and the decay in signal can be used for real-time, accurate oculomotor-neural recording based user intent classification, solving a machine learning challenge of combining disparate physiological signals, as well as temporal drifts in neural activity signal latencies, over time. Furthermore, it maximizes signal information, such that individual visual stimulus and gaze position signals can update the probability of overt attention for multiple objects.

In some embodiments, the processor 620 can include a Trainer 624 that is configured to present a training environment rendered through the user interface. The training environment can be configured to present a user with a set of predetermined controlled stimuli and record the ensuing eye movement and/or brain activity. This set of controlled stimuli and the evoked eye and brain activity corresponding to each of the controlled stimuli can then be stored in a memory 660 and used by a Model Builder 626 as training data to build statistical models that are tailor made for individual users. The Model Builder 626 can use one or more statistical tools like dimensionality reduction methods, feature extraction methods, machine learning tools to build classifiers etc. The models can be built, tested and cross-validated using the training data provided by the Trainer 624 and then can be used with new data from that particular user to achieve a high accuracy and speed of interaction with the user interface.

In some embodiments, the processor 620 can include a predictor 628 that can receive new data from a particular user, classify the data based on results from the model builder 626, and generate a prediction for user behavior using statistical tools like maximum likelihood estimation, maximum a posteriori estimation, etc. In some embodiments, the processor 620 can also include a Architecture Developer 632 that receives the eye-tracking and brain signal data as well as data from the other sub-components of the processor 620 (e.g., the trainer 624, the model builder 626, and the predictor 628). The Architecture Developer 632 may not be intended for real-time use, but for robust statistical analyses off-line towards prototyping potential BCI algorithmic detection architectures.

Usage and Implementation of a Hybrid BCI System

Figure 7:
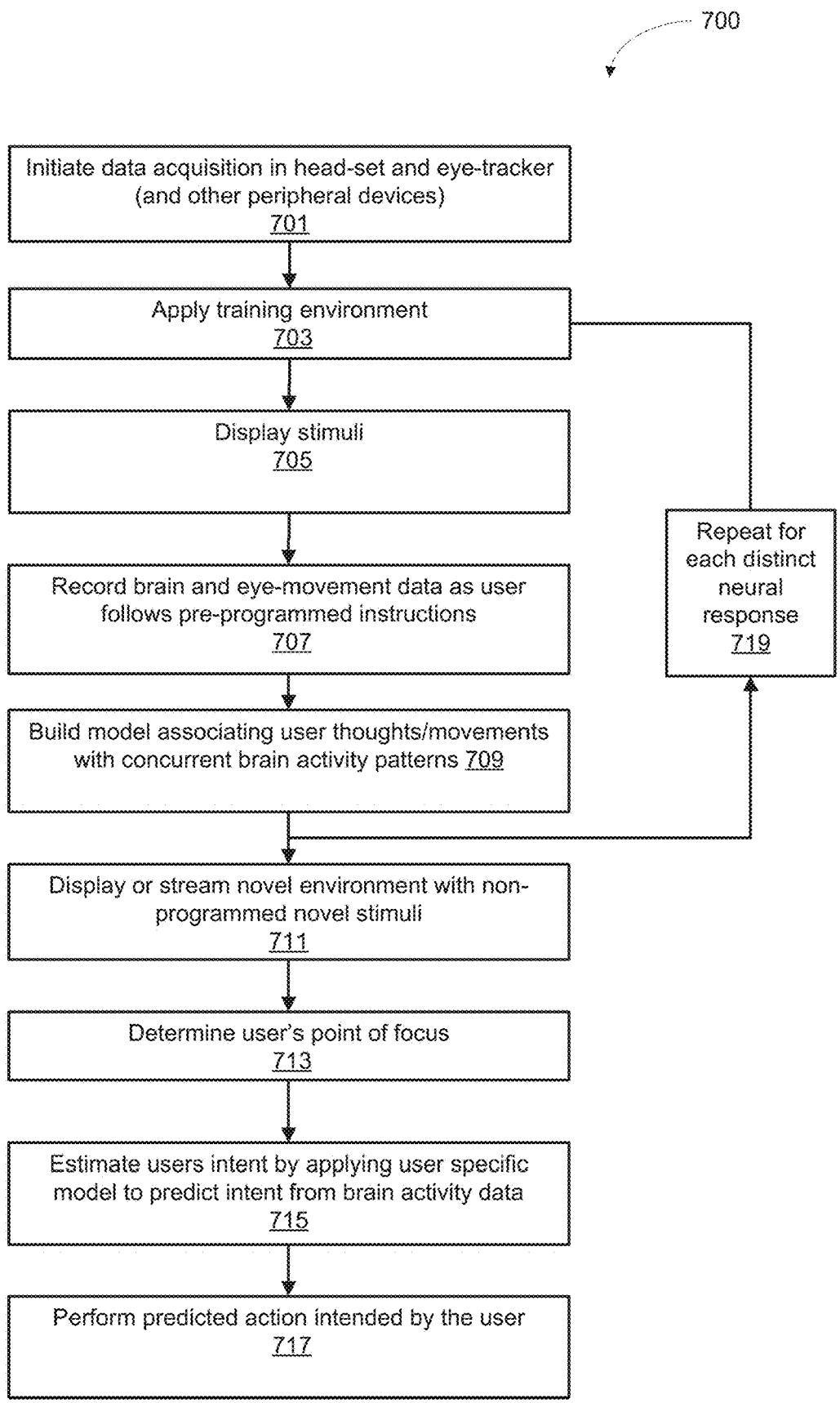
FIG. 7 shows an example process of operation of a hybrid Brain Computer Interfacing Device, according to an embodiment.

FIG. 7 shows an example process 700 of operation of an integrated hybrid Brain Computer Interfacing Device, according to an embodiment. In some embodiments, the process 700 includes an initial step 701 of initiating data acquisition and pre-processing for a particular user associated with a neural recording headset and an eye-tracker (and other peripheral sensors and/or actuators) at a time-point. This initiation and signal acquisition can be carried out by, for example, the Synchronized Event Logger 622. The process 700 also includes a step 703 of applying a training environment implemented by a trainer like the trainer 624 described above. The presentation of the training environment can include a set of pre-programmed, controlled stimuli displayed in step 705 and the ensuing eye movement and brain activity can be recorded in step 707. The presentation of varied, but controlled stimuli and collection of corresponding eye-movement and brain data can be repeated as shown by step 719 for a sequence of stimuli. The data can be fed into a model builder (e.g., the model builder 626), and the model can be updated with each set of new stimuli in the training set. Following which, the process 700 can include the presentation of a new environment that contains one or more novel stimuli, but may be associated with one or more of the preprogrammed stimuli that the system was trained with. Using the statistical models built by the model builder 626, the predictor 628 can then use any suitable statistical tool to generate predictions of user behavior like determining the point of focus in step 713 and estimating the user intent (i.e., to select or activate a particular symbol displayed) from the brain data in step 715. Based on the predictions, the process 700 then includes a step 717 to realize the user's intent in the user interface. For example, the step 717 can include selection of a letter in a speller, or selection of a character in a game, or the selection of ON functionality associated with a TV system that can be operated in an augmented reality system.

Hybrid BCI System Adaptations

Modes of Operation

The hybrid BCI systems 100 and/or 600 and other embodiments described herein can be configured as exogenous BCI systems that use the brain activity elicited by an external stimulus such as VEPs, auditory evoked potentials (AEPs), or P300 signals. Exogenous systems do not require extensive training since their control signals from neural activity can be easily and quickly set-up. Notably, the signal controls can be realized with fewer neural recording channels and can achieve a high information transfer rate of up to 60 bits/min.

In some embodiments, the hybrid BCI systems 100, 600 can be adapted to operate as endogenous BCI systems that are based on self-regulation of brain rhythms and potentials without external stimuli. For example, through neuro feedback training, the users learn to generate specific brain patterns which may be decoded by the BCI such as modulations in the sensorimotor rhythms. One advantage of an endogenous BCI is that the user can operate the BCI at free will and make or imaging voluntary movements that translate to movement in a pointing control feature like a cursor to any point in a two-dimensional space. Other features like hand gestures can also be trained with and used as cues to gain operational control over a user interface relieving any constraints on the user being restricted to the choices presented.

In some embodiments, the hybrid BCI systems 100, 600 can be used either in a synchronous (cue-paced) mode or in an asynchronous (self-paced) mode. Synchronous modes in BCIs can be of simpler design focusing on a predefined time window of brain activity triggered by a specific stimulus. In the synchronous mode the hybrid BCI system 100, 600 can analyze only the brain signals during the predefined time window and any brain signals outside the window can be ignored. Therefore, the user is only allowed to send commands during specific periods determined by the hybrid BCI system 100, 600. One advantage of a synchronous mode is that the onset of mental activity is known in advance and associated with a specific cue. Users may also inadvertently perform blinks and other eye or bodily movements, which can generate artifacts. As the brain signals outside a specified time window are not analyzed the misleading effects of these artifacts are avoided.

In some embodiments, the hybrid BCI systems 100, 600 can operate in the asynchronous mode, which continuously analyzes brain signals regardless of when the user acts. While more complex and hence computationally more demanding, the asynchronous mode can offer a more natural mode of human-machine interaction since the user does not have to wait for any external cues. In addition, richer data is gathered as the user interacts with the hybrid BCI system 100, 600 during the ordinary course of his or her actions.

Implementing High-Speed Signal Detection and Classification

The oculomotor-neural integrated hybrid BCI system described herein intelligently and flexibly exploits the strengths of oculomotor signals like signals from the video based eye-tracker 102 and neural signals including VEPs as selection and activation signals, respectively. One key component of this system is the high speed classification of eye movements. As described above with reference to the operation of the Synchronized Event Logger 622 the hybrid BCI system 600 can be configured to perform saccade detection in a lagless manner. For example, the hybrid BCI system 600 can filter gaze data with zero lag, using a non-linear generative model that estimates gaze as a dynamical system, with state and measurement models based on gaze kinematics and technical parameters of video based eye-trackers. Dual estimation, based on a dual Kalman filter, can be used in order to estimate hidden states of noisy gaze data and approximate the underlying system model. Thus, filtration of gaze data can be accomplished without introducing temporal lag. In addition, theoretical gaze kinematics models can estimate missing gaze data when camera sampling rate is lowered, or when transient artifacts occur. The hybrid BCI system 600 can also include a machine learning classification system that is automatically trained without an explicit training session enabling real-time detection of eye movements.

In some embodiments, lagless saccade detection can translate into an ability to detect saccade onset while eye movement is in progress. As shown, for example, in FIG. 5F, the detection latency (approximately 2 ms after saccade onset) can be shorter than a human's perception of the shift in visual scene (approximately 50-150 ms). Therefore, the hybrid BCI systems 100 and/or 600 can use the saccade onset vector as a prediction of where a user will look, and then update the user environment accordingly, before the user is aware of the shift in visual information. For example, during a program or a game, the user may plan to pause the game. As the user's eyes begin to shift direction towards a pause menu item, the saccade onset vector can be used to predict the intent to pause and select the pause menu before the user shift gaze to focus on the pause menu item. In some embodiments, the detection latency can be approximately 1.00 ms, 2.00 ms, 3.00 ms, 5.00 ms, 10.00 ms or 15.00 ms (or any time period there between).

Treatment of Artifacts

Artifacts are undesirable signals that contaminate brain activity and are mostly of non-cerebral origin. Since the shape of neurological phenomenon is affected, artifacts may reduce the performance of BCI-based systems. Artifacts can be physiological in origin or non-physiological or technical artifacts.

Physiological artifacts are usually due to muscular, ocular, and heart activity. Large disturbances in brain signals can arise from electrical activity caused by muscle contractions, which occur when patients are talking, chewing or swallowing. Other artifacts can be produced by blinking and other eye movements. Blinking makes generally high-amplitude patterns over brain signals in contrast to eye movements which produce low-frequency patterns. Artifacts associated with cardiac activity introduce a rhythmic signal into brain activity. Technical artifacts are mainly attributed to power-line noises or changes in electrode impedances, which can usually be avoided by proper filtering or shielding. Avoidance of physiological artifacts is difficult and rejection approaches suggest discarding the epochs contaminated by the artifacts. Automatic rejection may fail when artifact amplitudes are too small. Besides, rejection methodology leads to portions of the interaction that the user loses device control when artifact contaminated signals are discarded. Instead of rejecting samples, the artifact removal approach attempts to identify and remove artifacts while keeping the neurological phenomenon intact. Common methods for removing artifacts in neural are linear filtering, linear combination and regression, BSS and PCA. Instead of removing artifacts from recordings of brain signals, the system 100 and/or 600 can process artifacts to offer a communication path that can be used.

In some embodiments, the hybrid BCI systems 100, 600 can derive advantages from the artifacts to the benefit of user experience. For example, the systems 100, 600 can be configured to detect artifactual movements like eye blinks, jaw clenches, and other cardiac related changes. Detecting and classifying these artifacts gives scope to use the original neural signal for noise free applications. In some embodiments, the detected artifacts in the oculomotor-neural data can also be taken advantage of due to their known causality in the user's behavior. For example, artifacts like eye-blinks, jaw clenches, and facial expressions can be used as control signals to implement the action control feature, as disclosed below.

Embodiments of the hybrid BCI systems 100, 600 operated in the asynchronous mode can use an unsupervised classification system that incorporates a warm training set with a clustering model, and examination of Euclidean distance within n-dimensional feature space. The artifact identification approach which can be carried out by the uses a sliding window of data, over which features are calculated and then classified based on a clustering model over an n-dimensional space. Artifact intensity described over time can be used to classify through any suitable cluster based technique, for example classification methods based on the Euclidean distance of a data point to each cluster centroid.

Conventional BCI systems record data and at set time intervals, extract and process the recorded signals to determine user intent and user state. In some embodiments, the hybrid BCI system 100 and/or 600 described herein can be configured to process recorded data with each incoming sample to check for the presence of an "event" and using the presence of the "event" or lack thereof to trigger a chain reaction by the program. This can be further analysis of the data, changing the processing pipeline in anticipation of certain behaviors, or modifying the user's environment in some way. The process can be handled in a multithreaded environment by spinning off a processing pipeline on each incoming sample (from any device source) and passing that data through a classifier to determine its type.

Figure 8A:
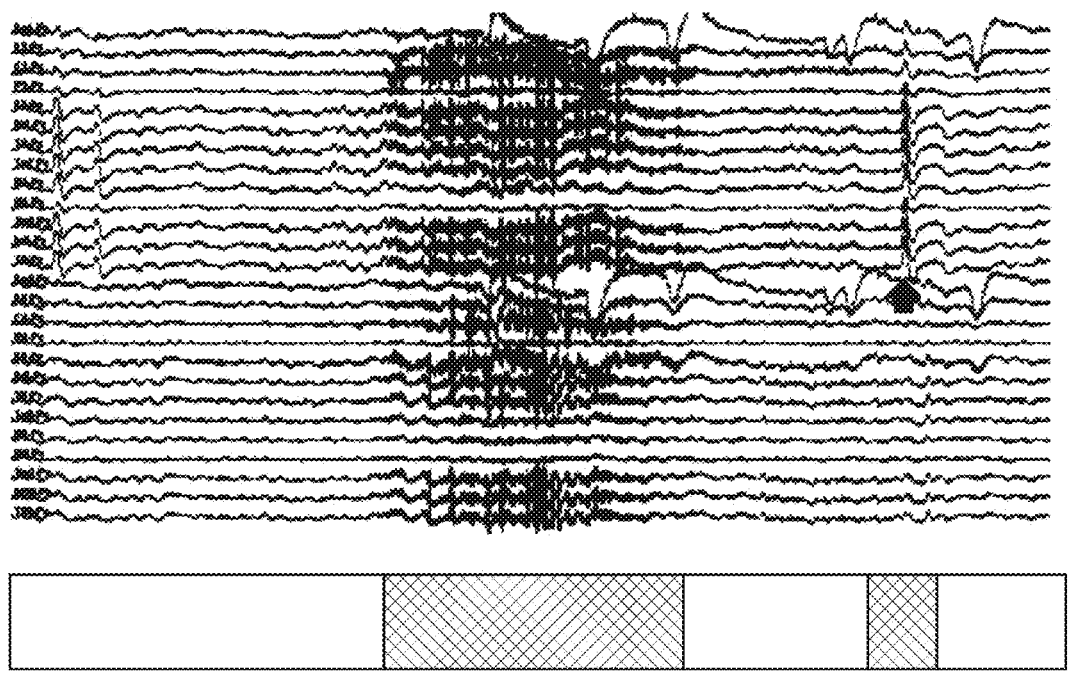
FIG. 8A shows an example set of brain signals recorded over time from a set of neural recording electrodes, using a hybrid BCI system according to an embodiment.

Events include eye blinks, event potentials, movement artifacts, excessive signal noise, and sudden drops in observed activity. Following the analysis stage, the interface can determine if a classifiable event has occurred, and if so, it can trigger a specific sequence of events. An example epoch of activity recorded is shown in FIG. 8A. For instance, when an eye blink is observed, the trigger can instruct the system to ignore incoming eye data for the next 5 milliseconds. When an event potential is observed, the trigger can instruct the system to identify the correlation between environment changes and the sudden presence of the event to identify which specific change affected the user's brain activity. Such example events are highlighted by the green and red bars in FIG. 8A.

Previous approaches to BCI implementation utilize a fixed time delay (i.e. 50 ms) after an event. After the fixed time delay passes, the user environment is changed, and the data pertaining to that time period is analyzed. In contrast, the system 10) and/or 600 according to some embodiments can implement an approach where no specific time delays or time periods are used, but instead incoming data is analyzed in a continuous manner. When the system identifies and classifies a specific type of event (as defined by the experimenter), the appropriate data extracted can be analyzed for additional information. For example, when an event is detected such as the one indicated in FIG. 8B, the detection can trigger a sequence of processes. Thus, the brain activity can act as a controlling signal and the detection of specific features can become actuators for additional events, actions and/or outcomes. This approach can be analogized to performing an action like clicking a mouse or pressing a button which directly triggers an immediate action as opposed to a polling model where, for example, a user might update their mailing address, and a phone book periodically to replace the old address with the new address.

User Interface Adaptations

As described herein, the user interface in the hybrid BCI system 100, 600 can be presented through an audio-visual display (for example, display 106 in FIG. 1). The user interface enables a user to focus and point at specific stimuli through the pointing control feature and select or deselect specific stimuli using the action control feature. In order to carry, this out, a user interface includes a selection set which is the group of available choices a user can make. Examples of selection sets can include letters/numbers on an alphanumeric matrix, or directional arrows, or groups of distinctly shaped icons or targets strategically arranged on a control display. The selection method describes how a command from a user will be interpreted by the BCI, either directly or indirectly. Direct selection allows a user to directly select any item from the selection set, while indirect selection requires an intermediary step before a user can make a selection.

Figure 9A:
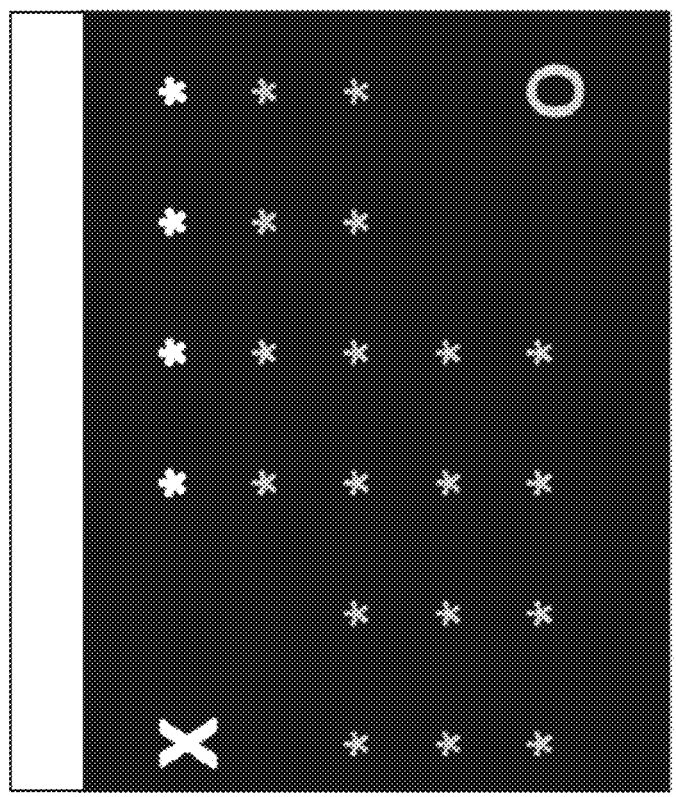
FIG. 9A illustrates instances of an example user interface before (left) and after (right) a user selection, according to an embodiment.

FIG. 9A shows two example layouts of a user interface including symbols (letters or numbers). In one example, all of the symbols are presented and flashed together at a time. In the second example, only one symbol (X) is shown in the flashed group while the others are hidden in the form of asterisks. In some embodiment, this second layout can improve processing times with reduced perceptual problems known to decrease neural activity based BCI classification accuracy. This layout may also be used to indicate a change in the user interface strategy, for example, the layout may indicate the entry into a 'hold-release mode' that is described further below.

The user interface can be configured to present the characteristics of the interface between the user and the BCI. The user interface can include three types of characteristics: (1) spatial, (2) sensory and (3) activation/deactivation. The spatial characteristics include the dimension, number and shape of the icons or targets. The sensory characteristics include the stimulus and feedback provided to the user, whether auditory, visual or somatosensory. The activation/deactivation includes the quality of the human/technology interaction.

The quality of interaction can be characterized by the effort (how difficult it is to use the BCI), displacement (how much movement is required to respond), flexibility (the number of ways in which the BCI can be used), durability (how reliable the BCI hardware is), maintainability (how easily the BCI can be repaired) and the method of activation or release (the ability to make/activate or stop/deactivate a selection and how that selection is made). Activation and deactivation can have distinct functionality, and using only activation as a action control input can be thought of as a trigger or momentary switch. In this case, only the activation causes an effect and the duration with which the activation is held does not alter the outcome. Using both activation and deactivation allows for more complicated control functionality and the control input can act as a button. For example, on a remote control for a television, you can activate and hold one of the volume keys to keep increasing the volume. In this case, holding a selection causes continued change, while releasing it keeps the current state.

Neural Activity Based Hold-Release Model

As described herein, the BCI systems 100, 600 can incorporate as part of their user interface a neural activity based BCI functionality in which the initial activation and the deactivation (hold-release) of targets in a neural activity based BCI can be separately controlled. This can allow the hybrid BCI systems 100, 600 to be used in applications that require indirect selection or applications that require quick changes between states. Further, it can allow confirmation-cancellation of a selected target by either holding the selection or switching attention to a release target.

Figure 8B:
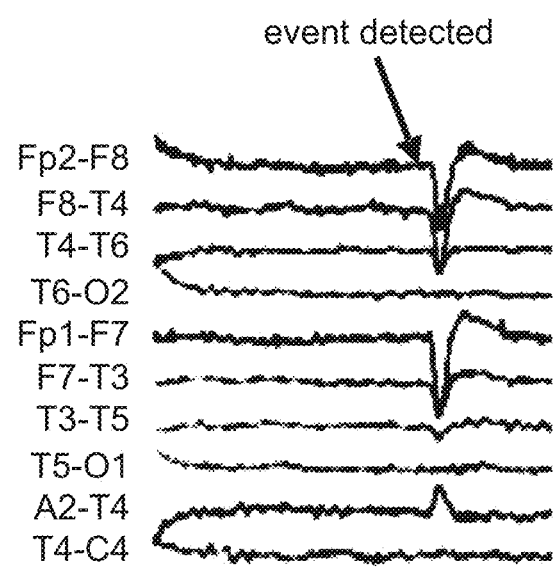
FIG. 8B shows an example set of neural brain signals recorded over time using a hybrid BCI system according to another embodiment.

In a potential real-world application, the targets on the BCI display can have different activation/deactivation characteristics. An example hybrid BCI user interface layout for a real-world application is shown in FIG. 8B. Some items can be hold-release enabled to allow fine adjustment, for example, reclining a wheelchair shown in the layout in FIG. 8B item B1, changing the temperature (item A3 and B3), or increasing the volume of a television (items C2 and D2). Safety-critical items, such as unlocking/locking a door (items D1 and E1), could require a hold-release confirmation-cancellation step, where a short hold period is required before activation. The remaining items would perform traditional discrete neural activity based actions, such as turning on lights or changing a television channel (C1, A2 and B2). Once the user selects a target with a hold-release response (for adjustment or confirmation) then the screen will change to a hold-release mode (FIG. 9B, right panel), in which only the previously selected target and a release target will be active and the rest of the targets on the BCI matrix will not be selectable. If the BCI correctly identified the desired target, the user will hold the selected target and the BCI will perform the action either until the user wanted the action to stop (relining wheelchair or changing television volume) or for a specified duration to confirm the selection (thereby preventing inadvertent activation of a safety-critical action). Thus, hold-release functionality expands the utility of neural activity based BCIs in ways that mirror the multiple control modes available on existing assistive technology.

During the holding process, the only information required by the BCI is when the user changes their selection (e.g., stops increasing/decreasing volume or recline a wheelchair). The binary nature of the release decision allows the BCI to make the decision from very few flashes instead of after multiple sequences of flashes. For the BCI user, this translates into a faster response time and a more continuous control than using the traditional neural activity based BCI approaches.

Neural Activity Based Mapping of Eliciting Stimuli

Traditional BCI systems (that observe how a user's brain activity changes in response to changes made to their environment) generally attempt to elicit all possible behaviors a user might have before analyzing all the data obtained at once, and from there determining user intent. In some embodiments, the hybrid BCI system 100 and/or 600 described herein can analyze the user's brain activity each time a change is made, and specifically using the information obtained from this analysis stage to inform the next change made to the environment. For example, if the user has 10 possible actions, then 10 changes can be made to the environment to observe which change eliciting the most ideal response (as defined by the program). Alternatively, in the hybrid BCI system 100 and/or 600, if the same user has the same 10 choices, the information obtained from the first change can be used to inform the next change to be made, and pre-emptively eliminate certain actions, thereby reducing the duration it takes to go from intent to action. Thus, knowledge of how the user's brain responds to each change made to the environment is not entirely required since each change informs on more than just one potential user intent. This reduces the amount of information to be recorded and instead intelligently determines what information will be needed to identify user intent, obtains that information quickly, and proceeds to creating the intended action.

In some embodiments, the hybrid BCI system 100 and/or 600, can also implement error correcting codes to carry out feature extraction from acquired neural signals to improve information transmission rates using the neural activity-based system. Additionally, the hybrid BCI system can utilize novel approaches to reduce refractory effects which are one of the main sources of noise in a neural activity based BCI system them by superimposing the targets on a suitable background or by using alternative stimulus types based on motion.

Dynamic Stimulus Detection and Tagging

Figure 9A:
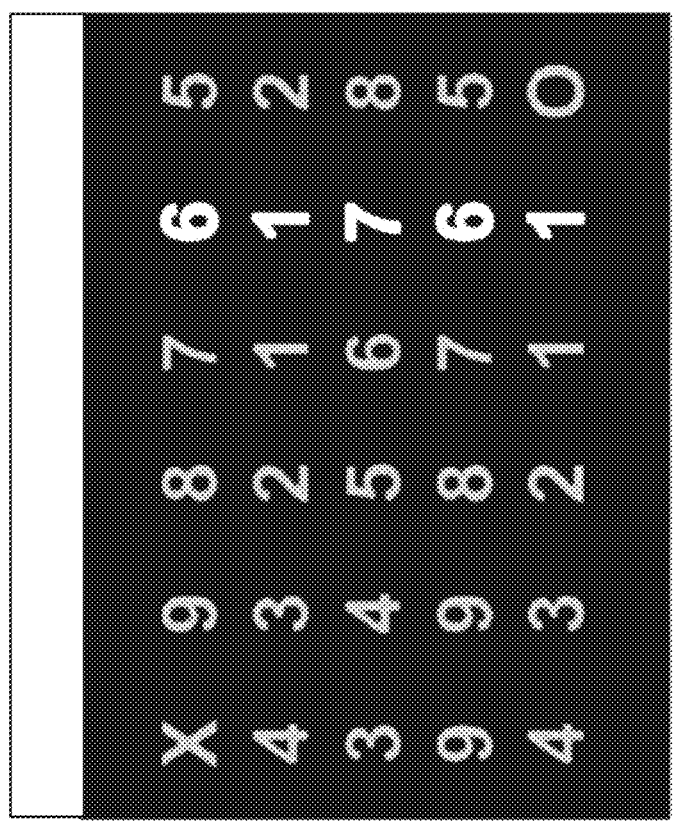
Figure 9B:
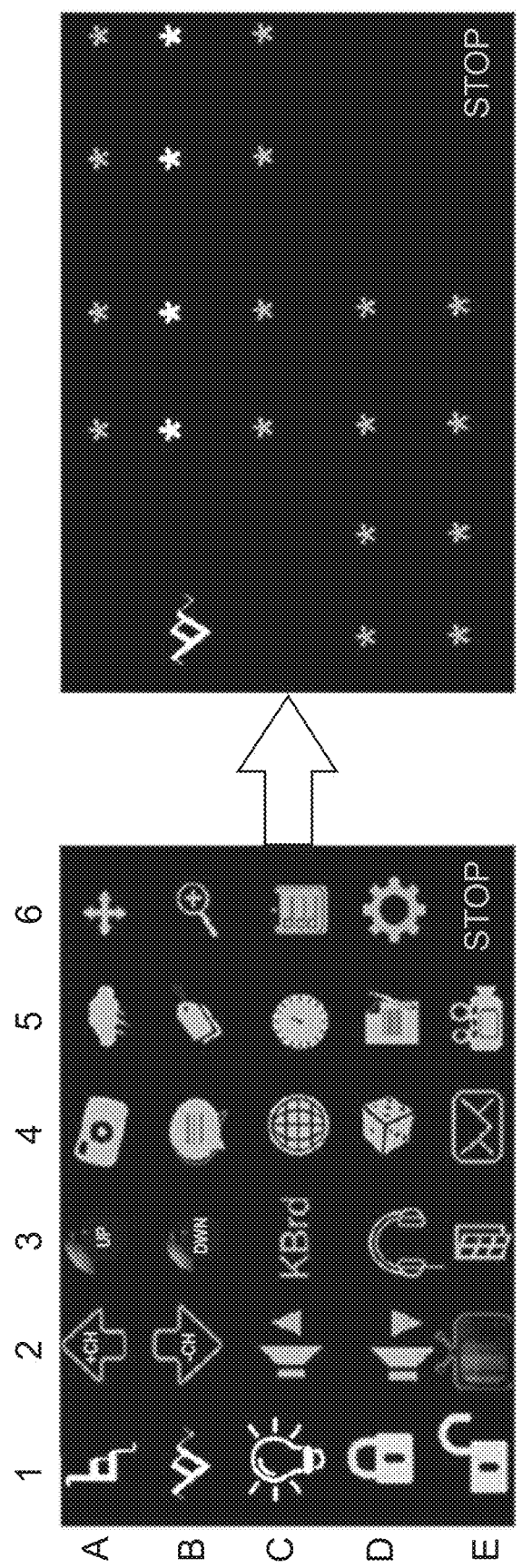
FIG. 9B illustrates instances of another example user interface following another layout, before and after user selection, according to another embodiment.
Figure 10:
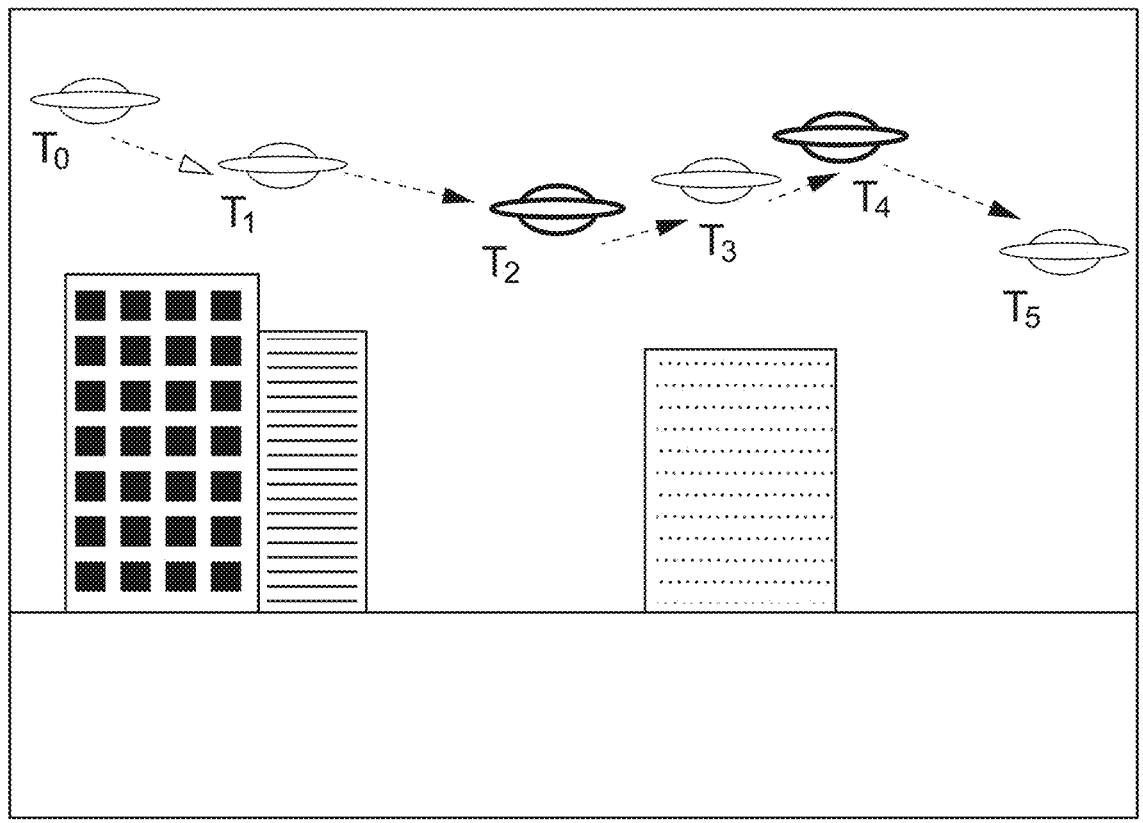
FIG. 10 shows several instances of an example user interface, illustrating the operation of dynamic tagging of a moving object in time.

In some embodiments, the hybrid BCI system 100 and/or 600 can incorporate dynamic stimuli or tag existing dynamic stimuli either in an augmented reality or a virtual reality presented in its user interface. That is, the hybrid BCI system 100, 600 can identify a moving stimulus and dynamically tag that stimulus to track its movements in time. An example implementation of such a dynamical identification and tagging is illustrated in FIG. 9.

The hybrid BCI system 100, 600 can detect the presence of a moving object and place selection tags onto the moving object. The tags can flash over the track timeline and maintain colocation with the object. The user can then use BCI selection to trigger an action with respect to that object. Alternatively, the hybrid BCI system 100, 600 can mainly be concerned with the start or end of the track. A time window of neural data near the track start or end could be examined to see if a neural activity was elicited. This would indicate that the newly object may be of interest to the user and could then trigger some action. In some embodiments, eye-tracking information can be used to see if a saccade was triggered by the objects initial movement to further bolster the assumption of object as interest prior to triggering the action. Such an action can be the dynamic tag placement as described above in addition to any others.

Feature Extraction and Model Building

Various thinking activities (cognitive tasks) result in different patterns of brain signals. In some embodiments, the hybrid BCI system 600 (and/or 100), can include a pattern recognition system that classifies each signal pattern into a class according to its features. The pattern recognition system extracts some features from brain signals that reflect similarities to a certain class as well as differences from the rest of the classes. The features can then be measured or derived from the properties of the signals which contain the discriminative information needed to distinguish their different types. As described above, the Model Builder 626 of the can use an array of statistical tools to build statistical models for features extracted from data corresponding with specific users, under specific user interfaces, coupled to specific hard ware peripheral, etc.

The information of interest in brain signals is typically hidden in a highly noisy environment, and brain signals comprise a large number of simultaneous sources. A signal that may be of interest may be overlapped in time and space by multiple signals from different brain tasks. For that reason, in many cases, it is not enough to use simple methods such as a band pass filter to extract the desired band power.

Brain signals can also be measured through multiples channels. Not all information provided by the measured channels is generally relevant for understanding the underlying phenomena of interest. Dimension reduction techniques such as principal component analysis or independent component analysis can be applied to reduce the dimension of the original data, removing the irrelevant and redundant information. Computational costs can thereby be reduced.

Brain signals are also inherently non-stationary, thus, in some embodiments it may be desirable to obtain time information about when a certain feature occurs. Some approaches that divide the signals into short segments can be used where the parameters can be estimated from each segment. One or more data transformations can be performed including methods like Fast-Fourier Transforms (FFT), Wavelet transforms or adaptive autoregressive components, or techniques like stationary subspace analysis (SSA) can be performed to reveal the non-stationary time variations of brain signals. SSA decomposes multivariate time series into stationary and non-stationary components. Multiples features can be extracted from several channels and from several time segments before being concatenated into a single feature vector.

Signal Classification and Prediction

The aim of the classification step in the hybrid BCI system 100, 600 is the recognition of a user's intentions on the basis of a feature vector that characterizes the brain activity provided by the feature step. Classification algorithms can be developed via either offline, online or both kinds of sessions. The offline session involves the examination of data sets, such as BCI competitions data sets, which are collected from an adaptive or closed-loop system. The statistics of the data may be estimated from observations across entire sessions and long-term computations may be performed. The results can be reviewed by the analyst with the aim of fine-tuning the algorithms. In some embodiments of the hybrid BCI system, the data can be processed online in a causal manner evaluating a real-world. The analytical algorithms used can be tested in an environment in which the user profile may change over time as a result of changes in motivation or involvement of the user, for example.

Classification algorithms can be calibrated by users through supervised learning using a labeled data set. However, brain signals as well eye-movement signals can be inherently non-stationary, with changes in their distinguishing characteristics over time. For example, the patterns observed in the experimental samples during calibration sessions may be different from those recorded during the online session. Alternatively, progressive mental training of the users or even changes in concentration, attentiveness, or motivation may affect the brain signals. In some embodiments, the hybrid BCI system 600 (and/or 100) described herein can use adaptive algorithms that can adapt to the changes in the distinguishing feature.

In some embodiments, the hybrid BCI system 100, 600 can use semi-supervised learning algorithms for detecting and classifying signals. The semi-supervised learning classifier can be initially trained using a small labeled data set, after which the classifier can be updated with on-line test data. This approach may reduce training time required by updating the classifier during an online session in a continuous manner.

In some embodiments, the hybrid BCI system 100, 600 may use unsupervised learning or reinforcement learning or a combination of these methods to detect and classify brain signals and/or eye-movement signals. Unsupervised methods can be used to find hidden structures in unlabeled data, in order to classify them. Some embodiments of the hybrid BCI device can use unsupervised methods that rely on techniques for co-adaptive learning of user and machine or covariate shift adaptation. Some embodiments can use reinforcement learning methods that are based on distinguishing neural signals elicited when a subject is aware of an erroneous decision. These feedback signals can be used as learning signals to prevent that error from being repeated in the future.

CONCLUSION

Figure 11:
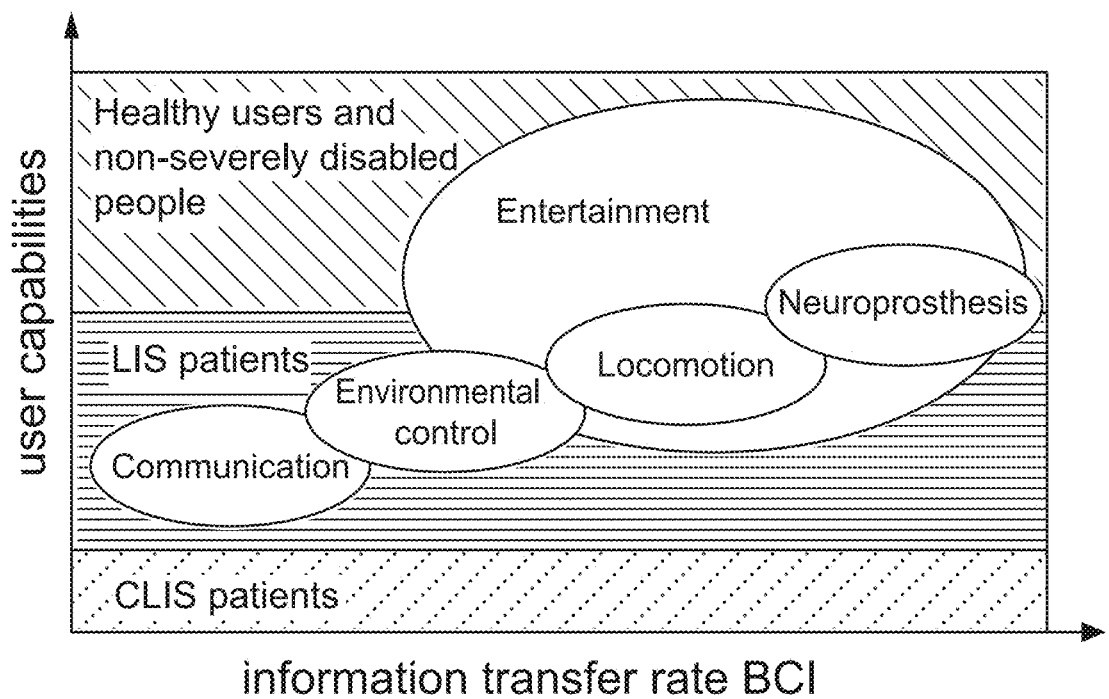
FIG. 11 shows an illustration of a space of utilization of BCI systems based on user capabilities and the type of BCI system.

In summary, systems and methods are described herein for use in the implementation of an integrated hybrid Brain Computer Interface operable by a user in real-time. The disclosed system includes an eye-movement tracking system to implement a pointing control feature and a brain activity tracking system to implement an action control feature. Both features are implemented through the presentation of a user interface strategically designed to enable high speed and accurate operation. Additionally, the disclosed systems and methods are configured to be hardware agnostic to implement a real-time hybrid BCI on any suitable platform to mediate user manipulation of virtual, augmented or real environments. FIG. 11 shows an illustration of the usage space of the inventive hybrid BCI system and methods.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. An apparatus, comprising:
   a display configured to present an interactive environment to a user;
   an eye-tracker configured to record eye-movement signals generated by the user;
   a neural recording device configured to record neural signals generated by the user;
   an interfacing device, operatively coupled to the display, the eye-tracker, and the neural recording device, the interfacing device including:
   a memory; and
   a processor operatively coupled to the memory and configured to:
      receive the eye-movement signals from the eye-tracker, and the neural signals from the neural recording device;
      generate and present a stimulus, via the interactive environment, to the user;
      determine a pointing control signal based on the eye-movement signals;
      determine an action control signal based on the neural signals;
      generate a composite set of data by combining a first portion based on the pointing control signal and a second portion based on the action control signal;
      provide the composite set of data to a machine learning model to determine a point of focus of the user, based on the composite set of data and
   identify an action intended by the user and based on the point of focus of the user.

2. The apparatus of claim 1, wherein:
   the eye-tracker is a video-based eye-tracker.

3. The apparatus of claim 1, wherein:
   the neural signals include electroencephalogram (EEG) signals including at least one of visually evoked potentials, auditory evoked potentials, motor imagery signals, Event Related Potentials (ERP), and brain state dependent signals.

4. The apparatus of claim 1, wherein the stimulus includes at least one of a visual, an auditory, and a haptic stimulus.

5. The apparatus of claim 1, wherein the stimulus includes a visual presentation of media via the display, and processor is further configured to define a set of portions of the display, and present the stimulus repeatedly, in one portion from the set of portions of the display, based on the point of focus of the user.

6. The apparatus of claim 1, wherein the processor is further configured to implement a lag-less filter and a classifier to process the eye-movement signals to determine the pointing control signal.

7. The apparatus of claim 1, wherein the processor is further configured to implement a dual Kalman filter and a classifier to process the eye-movement signals to determine the pointing control signal.

8. The apparatus of claim 1, wherein the processor is further configured to:
   train a gaze-kinematics model to:
      receive a first input associated with parameters of the user, a second input associated with the eye-tracker, and a third input associated with a stimulus from the set of stimuli;
      calculate, based on the first input, the second input, and the third input, a set of predicted gaze signals associated with an eye-movement of the user;
   identify a set of missing data points in the eye-movement signals;
   compute a set of replacement data points to replace the set of missing data points in the eye-movement signals, based on the set of predicted gaze signals calculated using the gaze-kinematics model; and
   incorporate the set of replacement data points to replace the set of missing data points and to generate updated eye-movement signals, the first portion being based on the updated eye-movement signals.

9. A non-transitory processor-readable medium storing code representing instructions to be executed by a processor, the instructions comprising code to cause the processor to:
   define a set of stimuli that can be presented to a user via an interactive user environment;
   present a stimulus from the set of stimuli to the user, via the interactive user environment;
   receive, from an eye-tracker a pointing control signal related to an eye-movement of the user and receive, from a neural recording device, an action control signal related to the eye-movement of the user;
   generate a composite data set by combining a first portion based on the pointing control signal and a second portion based on the action control signal;
   provide the composite data set to a machine learning model to identify a point of focus of the user;
   determine, based on the point of focus and the stimulus presented, an action intended by the user; and
   implement the action intended by the user via the interactive user environment.

10. The non-transitory processor-readable medium of claim 9, wherein the code to receive inputs includes code to cause the processor to:
    extract, from the action control signal received from the neural recording device, electroencephalogram (EEG) signals generated by the user, the EEG signals including at least one of visually evoked potentials, auditory evoked potentials, motor imagery signals, Event Related Potentials (ERP), and brain state dependent signals, the second portion being based on the EEG signals.

11. The non-transitory processor-readable medium of claim 9, wherein the code to cause the processor to determine the action intended by the user includes code to cause the processor to:

extract information related to the stimulus from the set of stimuli;
apply a first weight from a set of weights to the point of focus and a second weight from the set of weights to the information related to the presented stimulus, to generate a weighted representation of data; and
generate, based on the weighted representation of data, a prediction of the action intended by the user.

12. The non-transitory processor-readable medium of claim 9, wherein the code to cause the processor to determine the action intended by the user includes code to cause the processor to:
extract eye-movement signals from the pointing control signal received from the eye-tracker; and
implement a lag-less filter and a classifier to determine the first portion based on the pointing control signal.

13. The non-transitory processor-readable medium of claim 9, wherein the code to receive inputs includes code to cause the processor to:
train a gaze-kinematics model to:
receive a first input associated with parameters of the user, a second input associated with the eye-tracker, and a third input associated with a stimulus from the set of stimuli;
calculate, based on the first input, the second input, and the third input, a set of predicted gaze signals associated with an eye-movement of the user;
extract eye-movement signals from the pointing control signal received from the eye-tracker;
identify a set of missing data points in the eye-movement signals;
estimate a set of replacement data points to replace the set of missing data points in the eye-movement signals, based on the set of predicted gaze signals calculated using the gaze-kinematics model; and
incorporate the set of replacement data points to replace the set of missing data points to generate updated eye-movement signals, the first portion being based on the updated eye-movement signals.

14. The non-transitory processor-readable medium of claim 9, wherein the code to receive inputs includes code to cause the processor to:
train a gaze-kinematics model to:
receive a first input associated with parameters of the user, a second input associated with the eye-tracker, and a third input associated with a stimulus from the set of stimuli;
calculate, based on the first input, the second input, and the third input, a set of predicted gaze signals associated with an eye-movement of the user;
extract eye-movement signals from the pointing control signal received from the eye-tracker;
identify artifactual data points in the eye-movement signals;
estimate a set of replacement data points to replace the artifactual data points in the eye-movement signals, based on the set of predicted gaze signals calculated using the gaze-kinematics model; and
incorporate the set of replacement data points to replace the artifactual data points to generate updated eye-movement signals, the first portion being based on the updated eye-movement signals.

15. A method, comprising:
presenting, to a user, a stimulus via an interactive user interface;
receiving, from an eye-tracker, a pointing control signal associated with a eye-movement of the user;
receiving, from a neural recording device, an action control signal associated with the eye-movement of the user;
receiving information related to the stimulus;
generating a composite set of data by combining a first portion based on the pointing control signal and a second portion based on the action control signal;
providing the composite set of data to a machine learning model to identify a point of focus of the user, the point of focus being associated with the stimulus and the eye-movement;
determining, based on the point of focus, an action intended by the user; and
implementing the action via the interactive user interface.

16. The method of claim 15, wherein the presented stimulus includes a dynamic, visual-stimulus, the method further comprising:
detecting a movement of the dynamic, visual-stimulus;
tracking the movement of the dynamic, visual-stimulus; and
tagging the dynamic, visual-stimulus.

17. The method of claim 15, further comprising:
extracting eye-movement signals from the pointing control signal received from the eye-tracker; and
applying a lag-less filter to the eye-movement signals to determine the first portion.

18. The method of claim 15, further comprising:
training a gaze-kinematics model to:
receive a first input associated with parameters of the user, a second input associated with the eye-tracker, and a third input associated with a stimulus from the set of stimuli;
calculate, based on the first input, the second input, and the third input, a set of predicted gaze signals associated with an eye-movement of the user;
extracting eye-movement signals from the pointing control signal received from the eye-tracker;
identifying a set of missing data points in the eye-movement signals;
estimating a set of replacement data points to replace the set of missing data points in the eye-movement signals, based on the set of predicted gaze signals calculated using the gaze-kinematics model; and
incorporating the set of replacement data points to replace the set of missing data points and to generate updated eye-movement signals.

19. The method of claim 15, wherein the generating the composite set of data includes:
applying a first weight from a set of weights to the pointing control signal to generate the first portion, applying a second weight from the set of weights to the action control signal to generate the second portion, the composite set of data including a weighted representation of the pointing control signal and the action control signal.

20. The method of claim 15, further comprising:
training a gaze-kinematics model to:
receive a first input associated with parameters of the user, a second input associated with the eye-tracker, and a third input associated with a stimulus from the set of stimuli; and
calculate, based on the first input, the second input, and the third input, a set of predicted gaze signals associated with an eye-movement of the user;
extracting eye-movement signals from the pointing control signal received from the eye-tracker in response to;

computing filtered eye-movement signals, based on the eye-movement signals received from the eye-tracker and the predicted gaze signals calculated by the gaze-kinematics model, the first portion being based on the filtered eye-movement signals.

\* \* \* \* \*